United States Patent
Mota et al.

(10) Patent No.: US 7,670,631 B2
(45) Date of Patent: Mar. 2, 2010

(54) METHOD FOR THE PREVENTION OF MALARIA INFECTION OF HUMANS BY HEPATOCYTE GROWTH FACTOR ANTAGONISTS

(75) Inventors: Maria M. Mota, Lisboa (PT); Ana Rodriguez, Great Neck, NY (US); Silvia Giordano, Turin (IT); Margarida Cunha Rodrigues, Parede (PT)

(73) Assignee: ALFAMA—Investigação e Desenvolvimento de Produtos Farmacêuticos, Lda., Porto Salvo (PT)

( * ) Notice: Subject to any disclaimer, the term of this patent is extended or adjusted under 35 U.S.C. 154(b) by 884 days.

(21) Appl. No.: 10/795,456

(22) Filed: Mar. 9, 2004

(65) Prior Publication Data

US 2004/0185050 A1 Sep. 23, 2004

Related U.S. Application Data

(60) Provisional application No. 60/453,483, filed on Mar. 12, 2003.

(51) Int. Cl.
*A61K 36/48* (2006.01)

(52) U.S. Cl. .................................... 424/757
(58) Field of Classification Search .............. None
See application file for complete search history.

(56) References Cited

U.S. PATENT DOCUMENTS

| 6,214,344 | B1 | 4/2001 | Schwall et al. |
| 6,344,321 | B1 | 2/2002 | Ravin et al. |
| 6,887,499 | B2 * | 5/2005 | Bababunmi .............. 424/757 |

OTHER PUBLICATIONS

McGilvray et al., Blood, 96(9):3231-40, Nov. 1, 2000.*
Cunha-Rodrigues et al., Biotechnology Journal, 1(3);321-32, 2006.*
Carrolo et al.; Hepatocyte growth factor and its receptor are required for malaria infection; *Nature Medicine*, vol. 9(11) (Nov. 2003) pp. 1363-1396 (XP-002293600).

Lee et al.; Clindamycin as an antimalarial drug: review of clinical trials; *Antimicrobila Agents and Chemotherapy*, vol. 46(8) (Aug. 2002) pp. 2315-2320 (XP-002293805).
Maulik et al.; Role of the hepatocyte growth factor receptor, c-Met, in oncogenesis and potential for therapeutic inhibition; *Cytokine & Growth Factor Reviews*, vol. 13 (2002) pp. 41-59 (XP-002295576).
Kitamura et al.; Met/HGF receptor modulates bcl-w expression and inhibits apoptosis in human colorectal cancer; *British Journal of Cancer*, vol. 83(5) (2000) pp. 668-673m (XP-00229557).
Tacchini et al.; Hepatocyte growth factor signal coupling to various transcription factors depends on triggering of Met receptor and protein kinase transducers in human hepatoma cells HepG2[1]; *Experimental Cell Research*, vol. 256 (2000) pp. 272-281 (XP-002295578).
Mota et al.; Migration of *Plasmodium* sporozoites through cells before infection; *Science*, vol. 291 (Jan. 2001) pp. 141-144 (XP-002293602).
Mota et al.; Migration through host cells activates *Plasmodium* sporozoites for infection; *Nature Medicine*, vol. 8(11) (Nov. 2002) pp. 1318-1322 (XP-002293601).
Carter et al., "Plasmodia of Rodents," *Parasitic Protozoa*, vol. III, Gregarines, Haemogregarines, Coccidia, Plasmodia, and Haemoproteids, (1977), pp. 359-465.
Chen et al., "Database of traditional Chinese medicine and its application to studies of mechanism and to presecription validation," *British Journal of Pharmacology* (2006), 149, pp. 1092-1103.
Dluzewski et al., "Inhibition of invasion and intraerythrocytic development of *Plasmodium falciparum* by kinase inhibitors," Experientia 52, (1996), pp. 621-623 (*Birkhäuser Verlag Basel*).
Gazarini et al., "Interruption of the blood-stage cycle of the malaria parasite, Plasmodium *chabaudi*, by protein tyrosine kinase inhibitors," *Brazilian Journal of Medical and Biological Research*, vol. 36, No. 11, (2003), pp. 1465-1469.
Kraft et al., "Antiplasmodial activity of isoflavones from *Andira inermis*," Journal of Ethnopharmacology, vol. 73, (2000), pp. 131-135.
Langhorne et al., "Mouse models of blood-stage malaria infections: Immune responses and cytokines involved in protection and pathology," *Malaria Immunology*, Chem. Immunol., 2nd Edition, (2002), vol. 80, pp. 204-228 (Basel, Karger).

* cited by examiner

*Primary Examiner*—Marianne P Allen
(74) *Attorney, Agent, or Firm*—Wolf, Greenfield & Sacks, P.C.

(57) ABSTRACT

A method for the prevention of infection of humans by plasmodium parasites is provided. The method consists of the application of compounds that interfere with the infection of hepatocytes by *Plasmodium viax*.

5 Claims, 5 Drawing Sheets

Figure 5

Genistein effect on hepatic infection with
*Plasmodium berghei* sporozoites *in vitro*

METHOD FOR THE PREVENTION OF MALARIA INFECTION OF HUMANS BY HEPATOCYTE GROWTH FACTOR ANTAGONISTS

CROSS-REFERENCE TO RELATED APPLICATION

This application is based on and claims the benefit of U.S. Provisional Application No. 60/453,483, filed Mar. 12, 2003. The entire disclosure of this Provisional application is relied upon and incorporated by reference herein

FIELD OF THE INVENTION

This application relates to hepatocyte growth factor receptor antagonists and to inhibitors of signals induced by hepatocyte growth factor. More specifically, the application relates to the use of such compounds for the prevention of *Plasmodium falciparum* and *Plasmodium vivax* infections.

BACKGROUND OF THE INVENTION

The pathogenesis of malaria has been studied extensively and is described in many scientific publications and review articles [for recent examples see Miller et al., Nature 415:673-679, (2002)]. The causes of the disease are *Plasmodium falciparum* and to a lesser extent *Plasmodium vivax, Plasmodium malariae* and *Plasmodium ovale*. Death by malaria is almost exclusively caused *Plasmodium falciparum*. The parasites are transmitted by the vector *Anopheles gambiae*, which preferentially feeds on humans and is long lived. As the mosquito bites, sporozoites are injected into the skin. They travel to the liver, where they pass through several hepatocytes before they establish an infection and divide. Each sporozoite develops into tens of thousands of merozoites, which are released from the liver and invade erythrocytes. *Plasmodium falciparum* and *P. vivax* multiply in an asexual manner within erythrocytes. Over a period of two days each merozoite produces about 20 merozoites. The erythrocytes rupture and release merozoites which again invade erythrocytes. The disease begins with the asexual multiplication of the parasite inside erythrocytes. A few merozoites develop into gametocytes, which do not cause disease but transmit the infection to others through female *Anopheles* mosquitoes. *P. vivax* develops into gametocytes soon after the release of merozoites from the liver, while *P. falciparum* gametocytes develop much later.

Malaria is an important health problem in some parts of Asia and South America, and in particular in Sub-Saharan Africa. In any given year nearly 10% of the global population will suffer from malaria—600 million clinical cases. According to recent estimates at least one million deaths occur from malaria each year—a death from malaria every 30 seconds [Greenwood and Mutabingwa, Nature 415:670-672 (2002)]. In Africa malaria kills one out of twenty children before 5 years of age. Recently the malaria situation has deteriorated as a consequence of, among many other factors contributing to the increasing burden of malaria, the most important are the emergence of *P. falciparum* and *P. vivax* variants that are resistant to cheap and effective drugs, and the emergence of insecticide-resistant mosquitoes.

SUMMARY OF THE INVENTION

This invention aids in fulfilling these needs in the art. The evasiveness of malaria has made a definitive treatment difficult. Presented here is an agent and a method capable of preventing the spread or acquisition of malaria infection and of assisting in the prevention and treatment of such infection.

More particularly, this invention provides a method for inhibiting the activity of malaria in vivo, wherein the method comprises administering to a human host an antimalarial agent, which is capable of exhibiting a protective effect by preventing the initial replication of malaria parasites in the liver of an infected host such as humans. The antimalarial agent is comprised of at least one inhibitor of HGF activity, and optionally, an antimalarial drug, such as primaquine. The antimalarial agent is administered to the human in an amount sufficient to prevent or at least inhibit infection of hepatocytes by malaria in vivo or to prevent or at least inhibit replication or spread of a malaria parasites in vivo.

The present invention relates to the ability of hepatocytes to support the growth of parasites that cause the human disease malaria. *Plasmodium parasites* that cause human disease are *Plasmodium falciparum, Plasmodium vivax, Plasmodium malariae* and *Plasmodium ovale*. More specifically the invention reveals Met activation and downstream signals to be essential for the establishment of plasmodium infection. It has previously been known that *Plasmodium sporozoites* pass through several hepatocytes before they are able to establish a vacuole in hepatocytes in which they divide. It has not previously been known that the passage of sporozoites through hepatocytes is associated with the production of a well known cytokine, referred to as hepatocyte growth factor (HGF). HGF is known to be released as an inactive, single chain protein. It is activated by proteolytic cleavage that forms a disulfide bridge linked heterodimer. The heterodimer binds to and activates the receptor protein tyrosine kinase Met. The cytoplasmic domain of activated Met recruits a variety of proteins that transmit signals through several distinct pathways. These signals result in a variety of responses such as cell scattering, proliferation, tubulogenesis and invasive growth. The present invention reveals a novel Met mediated response of hepatocytes to HGF. Hepatocytes are rendered permissive by HGF to the invasion by sporozoites in a manner that allows their proliferation within a vacuole.

The present invention also provides a novel strategy for the prevention of plasmodium infections.

In preferred embodiments plasmodium infection of hepatocytes is prevented by molecules which interfere with HGF production by wounded hepatocytes.

Also suitable for the prevention of infection are molecules, which interfere with the proteolytic cleavage of HGF into its active form and molecules which sequester HGF and thereby prevent it from binding to hepatocytes via its receptor Met.

In another aspect, the invention reveals Met to be a target for drugs that prevent malaria infection.

In a preferred embodiment of the invention, malaria infection is prevented by molecules, which interfere with the binding of HGF to its receptor Met. Such molecules are antibodies specific for HGF which block its binding site for Met. Also in a preferred embodiment of the invention such molecules are antibodies against Met, or fragments of such antibodies, which block HGF binding but do not activate Met. In another embodiment of the invention such molecules are oligonucleotides (aptamers) which bind to Met but do not activate Met. In yet another embodiment of the invention such molecules are HGF variants that interfere with Met activation by HGF. Such variants include, but are not restricted to NR4.

In another aspect of the invention, plasmodium infection of hepatocytes is prevented by drugs, which interfere with signal transduction by activated Met. In a preferred embodiment of the invention such drugs are protein tyrosine inhibitors. An example of such a drug is genistein.

In another preferred embodiment such drugs are selective inhibitors of the protein tyrosine kinase Met. In preferred embodiments these inhibitors are small molecular weight compounds and are administered by the oral route or as suppositories.

BRIEF DESCRIPTION OF THE DRAWINGS

FIG. 5 shows Genistein effects on hepatic infection with *Plasmodium berghei* sporozoites in vitro.

DETAILED DESCRIPTION OF THE INVENTION

Figure 1:
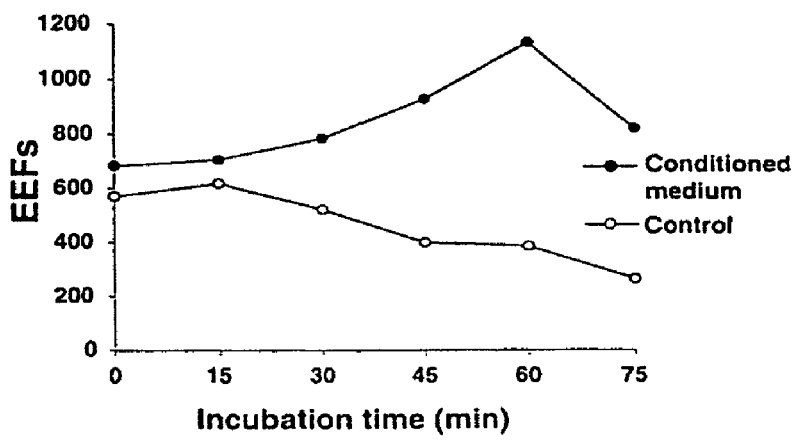
FIG. 1 shows that Sporozoite migration through cells and mechanical cell wounding induces the release of infection susceptibility inducing factors' (ISIF).
Figure 1:
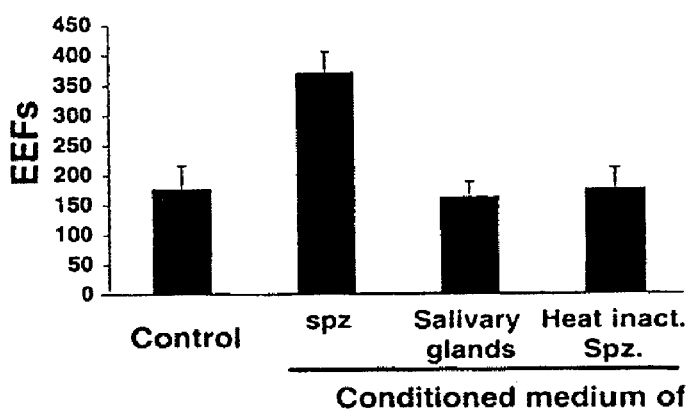
Figure 1:
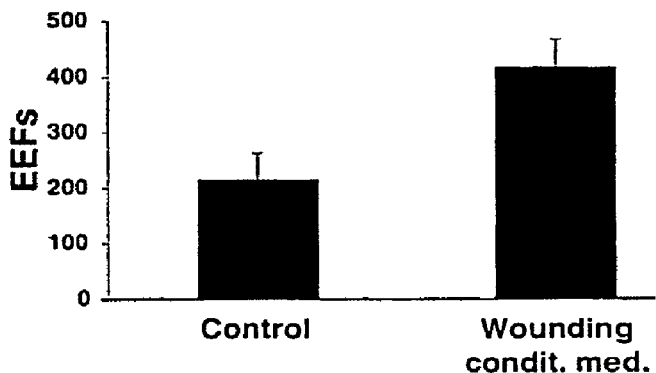

As used herein, the term "antimalarial agent" means a composition comprising one or more inhibitors of HGF activity. The term "inhibitor of HGF activity" means one or more compounds independently selected from HGF receptor antagonists, inhibitors of HGF-mediated signal transduction, and protein tyrosine kinase inhibitors. The inhibitor of HGF activity can be employed alone or in combination with each other. The inhibitors of HGF activity optionally can be combined with one or more known antimalarial drugs to form the antimalarial agent of the invention.

The present invention relates to the invasion of hepatocytes by malaria parasites. After transmission by a mosquito bite to a human host, malaria sporozoites find their way to the liver where each sporozoite can give rise to as many as 10,000 merozoites that are released into the blood. The invasion of hepatocytes is an obligatory step of malaria infection. Sporozoites can invade hepatocytes through disruption of the plasma membranes followed by parasite migration through the cells or, like intracellular bacteria and other parasites, through the formation of an internalization vacuole around the invading pathogen. Initially sporozoites pass through hepatocytes without forming an internalization vacuole. Sporozoites enter hepatocytes by breaching their plasma membranes, traverse the cytosol and leave the host cell which either dies or succeeds to repair the membrane. The molecular mechanisms underlying the passage of plasmodium through hepatocytes and the subsequent establishment of a parasitophorus vacuole are poorly understood. Vacuole formation by *Plasmodium yoelii* and *Plasmodium falciparum*, but not by the rodent malaria parasite *Plasmodium berghei*, is dependent on CD81, a tetraspin protein expressed by hepatocytes. CD81 is known to be a receptor for hepatitis C virus but it does not appear to interact with any ligand on the surface of sporozoites. Its role in hepatocyte invasion by certain plasmodium species remains to be elucidated [Silvie et al., Nature Medicine 9:93-96, (2003)]. Interestingly, sporozoites must traverse the cytosol of several cells before invading a hepatocyte by formation of a parasitophorous vacuole, which is indispensable for the differentiation into the next infective stage [Mota et al., Science 291:440-42, 2001)]. This finding suggests that hepatocytes wounded by sporozoites release one or more infection susceptibility inducing factors (ISIF) that render neighbouring hepatocytes susceptible to infection. An important aspect of the present invention is the discovery that a protein known as hepatocyte growth factor serves as ISIF in malaria infections.

I. HGF and its Receptor Met

Hepatocyte growth factor was discovered as a mitogen for hepatocytes [Michalopolous et al, Cancer Res., 44:441-4419 (1984); Rusasel et al J. Cell Physiol., 119:183-192 (1984); Nakamura et al., Biochem. Biophys. Res. Comm., 122:1450-1459 (1984)] and independently as a scatter factor that promotes the dissociation of epithelial cells and vascular endothelial cells [Stocker et al, Nature 327, 239-242 (1987)]. For simplicity the factor is referred to as HGF. HGF was first purified from the serum of hepatectomized rats [Nakamura et al., Biochem. Biophys. Res. Comm., 122:1450-1459 (1984)] and subsequently from rat platelets [Nakamura et al. Proc. Natl. Acad. Sci. USA, 83:6849-6493 (1986)] and from human plasma [Gohda et al., J. Clin. Invest. 81:414-419 (1988)]. The cDNAs encoding rat HGF, human HGF and a naturally occurring variant referred to as "delta5 HGF" were cloned [Miyazawa et al., Biochem. Biophys. Res. Commun., 163: 967-973 (1989); Nakamura et al. Nature 342:440-443 (1989); Seki et al., Biochem. Biophys. Res. Commun., 172:321-327 (1990); Tashiro et al., Proc. Natl. Acad. Sci. USA, 87:3200-3204 (1990); Okajima et al., Eur. J. Biochem., 193:375-381 (1990)]. Human HGF consists of an $\alpha$-subunit of 440 amino acids (M, 62 kDa) and a $\beta$-subunit of 234 amino acids (M, 34 kDa). It is produced as biologically inactive pro-HGF (728 aa) that is cleaved by proteases between Arg494 and Val495 to form a disulfide-linked heterodimer. The 62-kDa $\alpha$-subunit contains an N-terminal hairpin domain (about 27 aa) followed by four canonical kringle domains, which are 80-aa double-looped structures stabilized by three S-S bridges. The first kringle domain binds to a protein tyrosine kinase receptor, Met, which is described more in detail below. The hairpin loop and second kringle domain binds membrane-associated heparan sulfate proteoglycans with low-affinity. The 34 kDa $\beta$-subunit contains a serine protease-like domain very similar to that of the serine protease blood clotting factors but which has no protease activity. HGF shows 38% overall sequence identity with plasminogen and 45% identity with another cytokine known as macrophage stimulating protein (MSP). HGF binds to a protein tyrosine kinase receptor referred to as Met, while its close relative, MSP, binds to another protein tyrosine kinase receptor known as Ron.

HGF is secreted as single chain Pro-HGF. This HGF precursor is bound to proteoglycans that are associated with the extracellular matrix or with cell surfaces in the vicinity of the producer cells. Activation of the single chain precursor into the biologically active heterodimer by proteolytic cleavage between Arg494 and Val495 is a tightly controlled process [(for a review see Kataoka et al., Life XY 1:1036-1042 (2001)].

The enzymes first implicated in HGF activation were urokinase-type plasminogen activator (uPA) and tissue-type plasminogen activator (tPA). Subsequently three additional HGF activating enzymes have been identified, namely coagulation Factor XIIa, membrane type serine protease-1 (MT-SP1) also known as matriptase and HGF activator (HGFA). Each of these enzymes is under the control of endogenous inhibitor proteins. HGFA is the most effective HGF cleaving enzyme. Like HGF, HGFA is a heterodimer that is generated from a single chain Pro-HGFA by cleavage following Arg407. One of the HGFA cleaving enzymes is thrombin, an enzyme that is activated in injured tissues through the coagulation cascade. Active HGFA heterodimers are not inhibited by the major serum proteinase inhibitors, but are under the control of two proteins, HGA inhibitor type I (HAI-1) and HGA inhibitor type 2 (HAI-2), the latter being identical with placental bikunin (PB). HAI-1 is upregulated in injured and regenerating tissues. It is expressed at the cell surface where it binds and inhibits HGFA. Cytokines such as IL-1β induce shedding of the HGFA/HAI-1 complex by TNF-α converting enzyme (TACE) and the TACE-like metalloproteinases of the ADAM (a disintegrin and metalloproteinase) family of proteins. After shedding HGFA dissociates from HAI-1 and is then able to activate HGF. Thus, HAI-1 is not only an inhibitor but also a specific acceptor of mature HGFA, acting as a reservoir of this enzyme on the cell surface. HAI-1 is described in U.S. Pat. No. 6,465,622B2, published in Oct. 15, 2002, wherein it is claimed for its use as control factor for HGF and HGFA.

The HGF receptor Met was originally discovered as a component of an oncogenic fusion protein that was generated in a carcinogen treated sarcoma cell line [Cooper et al., Nature, 311:29-33 (1984)]. In normal cells the primary Met transcript produces a 150 kDa polypeptide that is glycosylated and then cleaved to form a S-S linked heterodimer. HGF and its receptor Met is subject of U.S. Pat. No. 5,648,273, published in July 15, which claims the use of the ligand-receptor for the diagnosis of proliferative disorders and diseases such as hepatitis and hepatocarcinogenesis.

The Met heterodimer consists of a β-subunit, that is highly glycosylated and entirely extracellular and a α-subunit with a large extracellular region and an intracellular tyrosine kinase domain. Met is a member of a superfamily of receptor tyrosine kinases (RTKs). The superfamily is divided into at least 19 families including the Her family (EGFR, Her 2, Her 3, Her 4), the insulin receptor family (insulin receptor, IGF-1R, insulin-related receptor), the PDGF receptor family (PGFRa and b, CSF-R, kit, Flk2), the Flk family (Flk-1, Flt-1, Flk-4), the FGF receptor family (FGF-R1, 2, 3, and 4) and others. Met and its close relative Ron form a distinct family of receptors for the ligands HGF and macrophage stimulating protein (MSP), respectively.

Upon HGF binding, c-Met undergoes autophosphorylation of specific tyrosine residues. While phosphorylation of Tyr1234 and Tyr1235 located within the activation loop of the tyrosine kinase domain activates the intrinsic kinase activity of c-Met, phosphorylation of Tyr1349 and Tyr1356 in the C-terminus generates a multisubstrate docking site for signal transducing proteins such as phosphotidylinositol 3-kinase (PI3K), phospholipase C-γ PLC-γ), src, Stat3, Grb2 and the Grb2 associated docking protein Gab1. Grb2 also interacts with Met through the adaptor protein Shc. Grb2 recruits the Ras nucleotide exchange protein SOS which activates the Ras-MAPK signaling pathway. Thus, the docking of signal transducers to the activated Met receptor initiate signaling through a variety of pathways. The c-terminal 26 amino acids of Met provide not only docking sites for signal transducers, but also regulate the enzymatic activity of Met. A mutation (M1250T) in the kinase domain bypasses the regulatory role of the C-terminal amino acids [Gual et al., Oncogene 20:5493-502 (2001)].

A variety of responses to HGF have been described in different Met expressing target cells. These responses include proliferation, programmed cell death, dissociation of cells, mutual repulsion, movement of cells through the extracellular matrix and branching morphogenesis. During embryogenesis interactions between HGF producing, mesenchymal cells and Met expressing, epithelial cells appear to be involved in the formation of a neuronal tissues. HGF gene knock out mice as well as Met gene knock out mice exhibit defects in the development of the placenta, liver and muscles and die between E13.5 and 15.5 [(Schmidt et al., Nature 373:699-702 (1995); Uehara et al., Nature 373:702-705 (1995); Bladt et al., Nature 376:768-771 (1995)]. In adult life, HGF-Met interactions are involved in wound healing, angiogenesis, and tissue regeneration. Not surprisingly Met activation by HGF has been implicated in the growth, invasion and metastasis of tumors. The biology of HGF and of its receptor Met is well described in several review articles [Maulik et al., Cytokine & Growth Factor Reviews, 13: 41-59 (2002)] and in numerous publications referenced therein.

Based on their biological properties, both HGF and HGF antagonists have been proposed to be useful for the treatment of a variety of diseases. The production of HGF and its therapeutic applications have been claimed in several patents. HGF has been isolated from blood on the basis of its high affinity for heparin (U.S. Pat. No. 5,004,805 published Apr. 2, 1991). Pegylation of HGF prolongs its clearance, reduces the dose required, and is thought to ameliorate side effects of HGF therapy (U.S. Pat. No. 5,977,310, published in Nov. 2, 1999). HGF levels may be increased by HGF degradation inhibiting polysaccharides such as heparin, hyaluronic acid, dextran, dextran sulfate, heparan sulfate, dermatan sulfate, keratan sulfate, chodroitin, or chondroitin sulfate (U.S. Pat. No. 5,736,506, published in Apr. 17, 1998). A HGF activating protease has also been claimed (U.S. Pat. No. 5,677,164, published in Oct. 14, 1997). Applications of HGF therapy include the treatment of arterial occlusive disease (U.S. Pat. No. 6,133,231, published in Oct. 17, 2000), the occlusive disease (U.S. Pat. No. 6,133,231, published in Oct. 17, 2000), the treatment of inflammatory bowel diseases (U.S. Pat. No. 6,319,899B1, published in Nov. 20, 2001), the enhancement of re-surfacing of blood vessels traumatized or damaged, for instance by vascular surgery or angioplasty (U.S. Pat. No. 6,133,234, published in Oct. 17, 2000). HGF has also been claimed to ameliorate side effects caused by commonly used immunosuppressants (U.S. Pat. No. 5,776,464, published in Jul. 7, 1998). Finally, the topical application of HGF gene containing vectors to blood vessels or other target organs has been described for a variety of therapeutic purposes (U.S. Pat. No. 6,248,722B1, published in Jun. 19, 2001). Met and downstream signal transduction pathways have long been regarded as attractive targets for cancer therapy. First, studies with tumor cell lines and tumor models in animals have shown that Met plays an important role in the invasive growth and in metastasis of cancer cells. Second, Met gene amplification has been observed in liver metastasis of colorectal carcinomas. Third, Met is overexpressed in several types of human tumors such as thyroid and pancreatic carcinomas. Fourth, germ line mutations in the Met gene are found in hereditary, papillary renal carcinoma, and somatic Met gene mutations are found in sporadic papillary carcinomas.

The present invention identifies a previously unknown function of the Met receptor, the inhibition of which represents a novel therapeutic application of Met antagonists. Signaling through Met renders hepatocytes permissive to productive invasion by malaria sporozoites. Met signaling is essential for the entry of sporozoites into hepatocytes via the formation of an internalization vacuole and/or the proliferation of sporozoites within vacuoles that are formed by the plasma membranes of hepatocytes. The discovery of this function of Met is the basis of a novel approach to the prevention of malaria infection. A further embodiment of the present invention is the use of compounds that prevent the establishment of a malaria infection by interfering with HGF mediated activation of Met or signaling events downstream of Met, that are involved in rendering hepatocytes permissive to the infection by malaria parasites. Several Met antagonists have been described in the literature and some have been claimed in patents for applications in the treatment of diseases that are caused at least in part by the excessive or aberrant function of Met. The previously claimed indications of Met antagonists are the treatment of malignant tumors. The potential application of Met antagonists for the treatment of infectious disease, and in particular of infections by malaria parasites becomes apparent through the present invention. The claim of the present invention is the use of Met antagonist for the prevention of human infections by malaria parasites. Known HGF antagonists are described in the following sections.

II. HGF Receptor Antagonists

A. HGF Variants

Various forms of HGF—both occurring naturally and generated by genetic manipulation of HGF encoding cDNA antagonize some or all Met functions. Uncleaved pro-HGF binds to but cannot activate Met. Several HGF isoforms are generated by differential splicing of primary HGF transcripts. These include NK1 (consisting of an N domain and the first kringle domain of HGF) and NK2 (consisting of an N domain and the first two kringle domains of HGF). Two additional variants discovered in the macaque endometrium and placenta, namely dNK1 and dNK2 are similar to the NK1 and NK2 isoforms, except that they encode proteins with a five amino acid deletion in the first kringle domain [Lindsey and Brenner, Mol Human Reprod. 8:81-87 (2002)]. NK1, and NK2 bind with high affinity to the HGF receptor Met and have been reported to act as HGF antagonists [Lokker and P. J. Godowski, J. Biol. Chem. 268: 17145-17150 (1993); Chan et al., Science 254:1382-1387 (1991)]. However, subsequent studies have shown that these HGF variants may act either as partial HGF agonists or as HGF antagonists depending on the cell context, the presence or absence of heparin, and the HGF function analyzed. In vivo studies with mice overexpressing transgenic HGF, NK1, NK2, HGF+NK1, or HGF+NK2 have revealed potential in vivo functions of HGF isoforms. Transgenic expression of HGF has a variety of phenotypic consequences such as enhanced liver growth, progressive glomerulosclerosis, disruption of olfactory mucosa, aberrant localization of muscle cells in the central nervous system and of melanocytes in the dermis and epidermis, precocious mammary lobuloalveolar development and susceptibility to tumor induction. Transgenic expression of NK1 produces a similar phenotype, while transgenic expression of NK2 exhibits none of the HGF and NK1 induced phenotypic characteristics. In HGF+NK2 bitransgenic mice NK2 antagonizes the pathological consequences of HGF overexpression and downregulates the subcutaneous growth of transplanted, Met expressing tumor cells. However, transgenic overexpression of NK2 promotes metastasis of these same tumor cells. Thus, NK2 antagonizes many of the responses to HGF, but shares with HGF the ability to dissociate (scatter) cells, a response that facilitates metastasis [Otsuka et al., Molecular and Cellular Biology 20:2055-2065 (2000)].

NK4, another HGF variant, is generated by a single cut digestion of HGF with elastase. NK4 contains the N terminal hairpin structure and four kringle domains. In contrast to NK1 and NK2, NK4 is a pure HGF antagonist [Date et al., FEBS Letters 420:1-6 (1997)]. Like the isolated HGF α chain, NK4 binds to Met but does not induce its autophosphorylation unless an isolated HGF β-chain is added. Because of its ability to antagonize HGF, administration of the NK4 protein or NK4 gene transfer [Hirao et al., Cancer Gene Ther 9:700-7 (2002); Maehara et al., Clin Exp Metastasis 19:417-26 (2002)] is being evaluated as a novel approach to the treatment of Met expressing cancers. Single chain HGF variants similar to NK4, which have been engineered to be resistant against proteolytic cleavage are described in U.S. Pat. No. 5,879,910, published in Mar. 9, 1999, and in U.S. Pat. No. 5,580,963 published in Dec. 3, 1996.

B. Soluble Met receptors

A soluble form of Met is released from cultured endothelial cells, smooth muscle cells, and various tumor cell lines. The soluble receptor is thought to counteract the activation of cell surface associated Met by HGF. Met-IgG fusion proteins have been generated which retain the ability to bind HGF with high affinity and thus are able to neutralize HGF activity.

C. Angiostatin

Angiostatin, an inhibitor of angiogenesis, is a fragment of plasminogen that contains 3-4 kringles domains. The anti-angiogenic effects of angiostatin are thought to be based on its ability to inhibit ATPase on the endothelial cell surface, and to interfere with integrin functions and with pericelluar proteolysis. Recent research indicates that the anti-angiogenic activity of angiostatin is at least in part due to its ability to neutralize the effects of HGF [Wajih and Sane, prepublished online in Blood, Oct. 24, (2002)].

Angiostatin, which has 47% sequence homology with HGF, binds to Met and prevents HGF mediated signaling in endothelial cells and smooth muscle cells. It inhibits the proliferation of these cells in response to HGF but not in response to other growth factors such as vascular endothelial cell growth factor (VEGF) or basic fibroblast growth factor (BFGF), which act through protein tyrosine kinase receptors other than Met. Thus angiostatin functions as a selective Met antagonist.

D. Anti-HGF Receptor Antibodies

While some anti-Met antibodies are receptor agonists others block ligand mediated receptor activation. Met blocking monoclonal antibodies and various derivatives of such antibodies have been developed by the company Genentech and are described in U.S. Pat. No. 6,468,529 B1 (published in Oct. 22, 2002), U.S. Pat. No. 6,214,344B1 (published in Apr. 10, 2001), U.S. Pat. No. 6,207,152B1 (published in May 1996) and of U.S. Pat. No. 5,686,292 (published in June 1995). These antibodies or derivatives of such antibodies are claimed to be useful for the treatment of cancer.

E. Met Selective Aptamers

Single stranded oligonucleotides with random sequences can form a large variety of structures. Oligonucleotides which bind to a particular target can be selected from large random oligonucleotide libraries by a method known as the SELEX process. Oligonucleotide ligands that selectively bind to Met and block ligand mediated Met activation have been identified by the company Gilead using the SELEX method. These HGF antagonists are described in U.S. Pat. No. 6,344,321 B1 (published in Feb. 2, 2002), in U.S. Pat. No. 5,843,653 (published in June 1995) and in U.S. Pat. No. 5,475,096 (published in June 1991).

III. Inhibitors of HGF-Mediated Signal Transduction

A. Met c-Tail Peptide

Modeling of the cytoplasmic domain of Met suggests that the c-terminal tail gets into contact with the catalytic pocket and thereby acts as an intramolecular modulator of the receptor. Bardelli et al designed peptides that correspond to sequences in the c-tail of Met. The peptides were rendered cell-permeable by extending them with sequences corresponding to internalization mediating sequences of the Antennapedia homeodomain. A Met tail peptide blocked ligand induced autophosphorylation as well as downstream Met signaling. The peptide also blocked signal transduction by Ron, a close relative of Met, but did not affect signaling by EGF, PDFG or VEGF through other protein tyrosine kinase receptors. Thus, the Met c-tail peptide is a selective Met/Ron antagonist.

B. Grb2 Antagonists

SH2 domains recognize phosphotyrosine residues (Tyr-P) with additional secondary binding interactions within two or three amino acids C-proximal to the Tyr-P residue. Differences in residues adjacent to Tyr-P generate differential affinity toward SH2 domain subfamilies. Thus, SH2 domains of particular sets of signal transducers can be selectively blocked by Tyr-P containing tripeptides. Inhibitors of SH2 domain interactions with phosphorylated tyrosine are described in U.S. Pat. No. 5,922,697, published in Jul. 13, 1999. Compounds in which the Tyr-P residue is replaced by phosphonomethyl phenylalanine or related structures, are resistant to degradation phosphatases. A variety of other modifications of the peptides increase the affinity for particular SH2 domains or increase the ability of the compounds to pass through plasma membranes to reach their intracellular targets [Yao et al J. Med. Chem., 42:25-35 (1999)]. Tripeptide based inhibitors of the Grb2 SH2 domain have been reported to block HGF mediated cell motility, matrix invasion, and branching morphogenesis. These same inhibitors have only a minor effect on HGF mediated cell proliferation. Inhibitors with particularly high affinity for the SH2 domain of Grb2 are described in U.S. Pat. No. 6,254,742B1, published in Jun. 12, 2001 as compounds that are useful for the treatment of cancer, metastasis, psoriasis as well as allergic, autoimmune, viral and cardiovascular diseases.

C. Inducers of Gab1 Phosphorylation

Phosphorylation of serine/threonine residues of the Grb2 associated binder 1 (Gab1) by PKC-α and PKC-β1 provides a mechanism for the downregulation of Met signals. Inhibition of serine/threonine phosphatases PP1 and PP2A by okadaic acid results in the activation of serine/threonine kinases such as PKCs, and in the hyperphosphorylation of the serine/threonine residues of gab1. The concomitant hypophosphorylation of tyrosine residues prevents Gab1 from recruiting PI 3 kinase to Met [Gual et al., Oncogene 20:156-166 (2001].

D. Dominant Negative Src Variants

Src binds via its SH2 domain to phosphorylated tyrosine residues of ligand activated Met. The mutant receptor MET M1268T binds src constitutively and NIH3T3 cells expressing the mutant receptor gene form tumors in nude mice. Transfection of dominant negative src constructs into these cells was reported to retard their growth, and to downregulate the phosphorylation of the focal adhesion kinase (FAK) and of paxicillin, but had no effect on Grb2 binding or PLC-γ phosphorylation [Nakaigawa et al., Oncogene 19:2996-3002 (2000)].

E. PI3K Inhibitors

The binding of PI3K to Met is unusual in that it does not involve the canonical motif YXXM but a novel motif YVXV. Although the novel motif has low affinity for the N- and C-terminal SH2 domains of the p85 subunit of PI3K, two closely spaced YVXV motifs in the c-tail of Met represent a docking site for PI3K. The binding is inhibited by synthetic phosphopeptides. The PI3K-mediated signal appears to be essential for HGF induced cell scattering (cytoskeletal reorganization, loss of intercellular junction, cell migration) and morphogenesis. Wortmannin, an inhibitor of PI3K, inhibits Met induced branching of renal cells on a collagen matrix. PI3K signals appear not to be essential for cell transformation, but do contribute to metastasis.

F. NFkB Inhibitors

In liver cells HGF stimulates NF-kappaB DNA binding and transcriptional activation via the canonical IkappaB phosphorylation-degradation cycle and via the extracellular signal-regulated kinase ½ and p38 mitogen-activated protein kinase cascades. Studies with NFkB inhibitors indicate that HGF induced NFkB activation is required for proliferation and tubulogenesis, but not for scattering nor for the antiapoptotic function of HGF [(Muller et al., Mol Cell Biol 22:1060-72, (2002)].

G. Inhibitors of Small GTP-Binding Proteins

Inhibition of Ras interferes with the spreading, actin reorganization, and scattering of epithelial cells. Dominant negative Rac abolishes HGF induced spreading and actin reorganization in non-small cell lung cancer cells. Microinjection of Rho inhibits HGF induced spreading and scattering but not motility.

H. Hsp90 Antagonists

The chaperone Hsp90 stabilizes many proteins involved in signal transduction. The chaperone appears to be required for the stability and function of a variety of mutated or aberrantly expressed signaling proteins that promote the growth and/or survival of cancer cells. Hsp90 client proteins include mutated p53, Bcr-Abl, src, Raf-1, Akt, ErbB2 and hypoxia-inducible factor 1α (HIF-1α). The benzoquinone ansamycin compounds geldanamycin and herbimycin and the structurally unrelated radicicol block the N-terminal nucleotide binding pocket of HsP90 and cause the degradation of Hsp90 client proteins, many of which are involved in tumor progression. One Hsp90 inhibitor, 17-allylaminogeldanamycin (17AAG), is currently in phase I clinical trial, and a novel oxime derivative of radicicol (KF58333) is in preclinical evaluation [(Soga et al., Cancer Chemother Pharmacol 48: 435-45, (2001)].

Recent research has shown that Met is a Hsp90 client that is particularly sensitive to geldanamycin or related compounds. At nanomolar concentrations, geldanamycins downregulates Met protein expression, inhibit HGF-mediated cell motility and invasion and revert the transformed phenotype of cells expressing HGF and Met or constitutively activated Met mutants. Signaling pathways downstream of Met appear to be even more sensitive to Hsp90 inhibitors. Geldanamycins inhibited HGF-mediated plasmin activation at femtomolar concentrations which is nine orders of magnitude below their growth inhibitory concentrations. Interestingly, radicicol has been reported to be moderately active against *Plasmodium berghei* in mice [Tanaka et al., J. Antibiot. 51:153-60 (1998)]. However, this activity is likely not related to Met inhibition [Tanaka et al., J Antibiot 10:880-8 (1999).

IV. Protein Tyrosine Kinase Inhibitors

The reversible phosphorylation of tyrosine residues on proteins is an important mechanism of signal transduction. A large variety of natural and synthetic compounds are known to be tyrosine kinase inhibitors. Almost all of these inhibitors block protein kinases by blocking the ATP pocket of the enzymes. Therefore, many have a broad spectrum of activity not only against tyrosine kinases but also against serine/threonine kinases and/or other ATP utilizing proteins.

1. General Protein Kinase Inhibitors

The Indrocarbazole K252a was first isolated from the culture broth of Actinomadura and later from Nocardiopsis in a screen for antagonists of Ca2+-mediated signaling. K252a inhibits serine/threonine protein kinases such as various isoforms of protein kinase C (PKCs), cAMP and cGMP dependent kinases as well as protein tyrosine kinases, in particular those of the Trk and Met families. K252a inhibits Met mediated signals at nanomolar concentrations. The compound inhibits Met autophosphorylation and prevents activation of its downstream effectors MAPKinase and Akt. It prevents HGF-mediated scattering in MLP-29 cells, reduces Met-driven proliferation in GTL-16 gastric carcinoma cells, and reverses Met mediated transformation of NIH3T3 fibroblasts. K252a and related compounds are promising leads of drugs that may be used against Trk and Met driven cancers [Morotti et al., Oncogene 21:4885-4893, (2002)]. Conceivably, K525a may serve as a lead in the development of Met specific inhibitors.

2. Inhibitors with Selectivity for Protein Tyrosine Kinases

Several classes of compounds are known protein tyrosine kinase inhibitors. Several such compounds have been isolated from plants or microorganisms and have been extensively used for research purposes. The best known are genistein, lavendustin A, tyrphostin 47, herbimycin, staurosporin and radicicol. Herbimycin A is a benzoquinoid ansamycin antibiotic that inhibits a broad spectrum of protein tyrosine kinases by covalently interacting with their kinase domains. Staurosporin is an indole carbazole antibiotic which inhibits a broad spectrum of kinases including scr family members, and serine/threonine kinases. More recently a large number of protein tyrosine kinase inhibitors have been synthesized and are claimed in several patent applications. 1) bis monocyclic, bicyclic or heterocyclic aryl compounds (PCT WO 92/20642); 2) vinylene-azaindole derivatives (PCT WWO 94/14808); 3) 1-cyclopropyl-4-pyridyl-quinolines (U.S. Pat. No. 5,330,992). 4) styryl compounds (U.S. Pat. No. 5,217, 999); 2) styryl-substituted pridyl compounds (U.S. Pat. No. 5,302,606); 5) quinazoline derivatives (EP Application No. 0 566 266A1 and U.S. Pat. No. 6,103,728); 6) selenoindoles and selenides (PCT WO 94/03427); 7) tricyclic polyhydroxy-lic compounds (PCT WO 92/21660); 8) benzylphosphonic acid compounds (PCT WO 91/15495); 9) tyrphostin like compounds (U.S. Pat. No. 6,225,346B1); 10) thienyl compounds (U.S. Pat. No. 5,886,195). 11) benzodiazepine based compounds with some selectivity for src and FGF-r tyrosine kinases (U.S. Pat. No. 6,100,254, published in Aug. 8, 2000). Tyrosine kinase inhibitors from various classes are claimed for the treatment of cancers that are driven by tyrosine kinases such as Met as well as HER2, EGFR, IGFR, PDGFR, src and KDR/FLK-1. None of the known tyrosine kinase inhibitors are selective for Met. However, it is conceivable that a Met specific inhibitor can be developed in the future. This optimism is based on the fact that several compounds have been synthesized which inhibit a limited set of protein tyrosine kinases one of which is approved for cancer therapy and several of which are in clinical development. These compounds include: 1) The pyrazole pyrimidine PP1 shows selectivity for lck and src kinases over ZAP-70, JAK2 and EGF receptor kinases. 2) STI-571 (GLEEVEC®) inhibits all forms of abl, PDGF receptor, and c-kit tyrosine kinases. 3) ZD1839 is a synthetic anilinoquinazoline with some selectivity for the EGF receptor. 4) OSI-774 is another orally active quinazoline derivative with some selectivity for the EGF receptor. 5) 4-anilinoquinazoline derivatives show selectivity for the VEGF-R (U.S. Pat. No. 6,291,455B1, published in Sep. 18, 2001). 6) SU101 shows selectivity for the PDGF receptor, but its antiproliferative effects are in part due to an ring-opened metabolite which inhibits dihydro-orotate dehydrogenase, a mitochondrial enzyme crucial to pyrimidine biosynthesis. 7) Aryl and heteroaryl quinazoline compounds show selectivity for CSF-R (U.S. Pat. No. RE 37,650 E, published in Apr. 9, 2002.8) SU 5416, a VEGF receptor (Flk1/KDR) antagonist was designed on the basis of crystallographic studies of the indolin-2-one pharmacophore and the FGF receptor tyrosine kinase domain. 9) Bis mono- and bicyclic aryl and hetero aryl compounds show selectivity for EGFR and PDGFR (U.S. Pat. No. 5,409,930). 10) Piceatannol (3,4,3,5V-tetrahydroxy-trans-stilbene) shows selectivity for syk and lck, but also inhibits serine/threonine kinases and ATPase. 11) Several compounds that are based on benzodiazepines show some selectivity for the non-receptor tyrosine kinase src and for the FGF-R tyrosine kinase receptor family. These examples show that compounds with selectivity for one or a few tyrosine kinases can be generated.

V. Anti-Malarial Effects of Protein Kinase Inhibitors

Like plants the related apicomplexan parasites such as plasmodium appear not to produce protein tyrosine kinases. A few reports suggest that protein tyrosine phosphorylation occurs in plasmodium (see section A below). However homology searches have failed to detect any sequences related to the known protein tyrosine kinase families. Therefore it is conceivable that antimalarial effects of protein tyrosine kinase inhibitors are due to the inhibition of the enzymes that are produced by the human host. A variety of quinazoline derivatives have been reported to have antimalarial activity. These compounds include 2,4-diamino-6(3,4-dichlorobenzylamine quinazoline (PAM1392 [Thompson et al. Exp. Parasitol 25:32-49, 1969)], 2,4-diamino-6-[93,4-dichlorobenzyl0-nitrosoamino]-quinazoline (CI-679) [Schmidt and Rossan, Am. J. Trop. Med. Hyg. 28:781-92, (1979)], several other 2,4-diamine-6-substituted quinazoline derivatives Elslager and colleagues [Elsager et al., J. Med. Chem. 21:1059-70, (1978)] and by Chinese scientists [Gy et al., Xao Xue Bao 19:108-18, (1984), Yao et al., Yao Xue Bao 19:76-8, (1984)]. The antimalarial activity of 2,4-diamino-5-methyl-693,4,5-trimethoxyanilinomethyl) quinazoline salts is described in U.S. Pat. No. 4,376,858, published in Mar. 15, 183. One possible mode of action of quinazoline derivatives against plasmodium are inhibition is the inhibition of tyrosine kinases (U.S. Pat. No. 6,103,728, published in Aug. 15, 2000).

A) Inhibition of Plasmodium Protein Kinases

1) Dluzeski and Garda reported that several protein kinase inhibitors (staurosporin, genistein, methyl 2,5-dihydroxycinnamate, tyrphostin B44 and B46, lavendustin A and RO3) inhibited the erythrocytic cycle of *plasmodium falciparum* [Dluzewski and Garda, Experientia 52:621-623, (1996)]. With the exception of staurosporin, a strong serine/threonine kinase inhibitor, these compounds preferentially inhibit protein tyrosine kinases. These inhibitors prevented the development of the parasites within erythrocytes and/or invasion. Because of the broad spectrum of activities of these inhibitors it is not clear whether inhibition of a protein tyrosine kinase played any role in the observed effects, nor is it clear whether the target proteins were derived from the erythrocytes or from the parasites.

2) While screening artemisinin like compounds from microorganisms, Tanaka and colleagues identified seven fungal metabolites with antimalarial activity. One of these compounds, radicicol, a broad spectrum protein kinase inhibitor was moderately active against *Plasmodium berghei* in mice [Tanaka et al., J. Antibiot 51:153-60, (1998)].

3) More recently Sharma reported that a membrane bound PTK activity was increased during maturation from the ring stage to the trophozoite stage. Inhibition of the PTK activity by chloroquine was proposed to represent one possible mechanism of action of this drug against the parasite [Sharma and Mishra, Indian J. Biochem. Biophys. 36:299-304 (1999); Sharma, Indian J. Exp. Biol. 38:1222-6 (2000)].

B) Inhibition of Human Protein Tyrosine Kinases

A variety of pathogenic effects of plasmodium are mediated by protein tyrosine kinases of the human host and thus can be inhibited by protein tyrosine kinase inhibitors. Several examples have been reported in the literature.

1) Adhesion of infected erythrocytes to vascular endothelium involves the binding of *P. falciparum* membrane protein 1 (PfEMP1) to CD36 that is expressed by endothelial cells of the host. A signal mediated by CD36 is essential for adhesion. The pyrazolopyrimidine PP1, a selective inhibitor of src and lck kinases, inhibits this signal and prevents adhesion [Yipp et al., Blood online, (2002)].

2) CD36 and CD36 mediated, protein kinase dependent signals are also involved in the nonopsonic clearance of *P. falciparum* infected erythrocytes by monocytes and macrophages. Both genistein and selective ERK and p38 MAPK inhibitors (PD98059 and SB203580, respectively) reduced the uptake of infected erythrocytes to almost the same extent as CD36 blockade [McGilvray et al., Blood 96:3231-40, (2000)].

3) Glycosylphosphatidylinositol (GPI) is a major toxin of *Plasmodium falciparum*. Malarial GPI induces rapid onset tyrosine phosphorylation of multiple intracellular substrates within 1 min of addition to cells. These signals are involved in the upregulation of parasite adherence and in the induction of nitric oxide (NO) release by macrophages and endothelial cells. Both adherence and NO release are prevented by the tyrosine kinase antagonists tyrphostin and genistein [Tachado et al., J Immunol 156:1897-1907, (1996); Schofield et al., J. Immunol. 156:1886-96].

In previous work the protein tyrosine kinase receptor Met has not been implicated in malaria infections. The present invention identifies the protein tyrosine kinase Met as a crucial mediator of hepatocyte susceptibility to infection by malaria sporozoites.

VI. HGF Related Anti-Malarials

A. Sulfated Polysaccharides

As mentioned above, HGF levels may be increased by HGF degradation inhibiting polysaccharides including dextran sulfate, heparan sulfate, dermatan sulfate, keratan sulfate, chondroitin, or chondroitin sulfate. The combination of sulfated polysaccharides, such as sulfated curdlan, dextrin sulfate, chondroitin sulfate, heparin, carageenan) with quinine for the treatment of malaria is described in U.S. Pat. No. 5,780,452, published in Jul. 14, 1998. The proposed strategy is based on the ability of sulfated polysaccharides to inhibit the invasion of human erythrocytes by malarial parasites. The present invention raises concerns regarding this strategy, since sulfated polysaccharides may increase HGF levels by inhibiting its degradation, a fact described in U.S. Pat. No. 5,736,506, published in Apr. 17, 1998. Therefore sulfated polysaccharides are excluded from the antimalarial agent of this invention.

EXAMPLES

Example 1

Release of 'Infection Susceptibility Inducing Factors' (ISIF) by Hepatocytes Incubated with *Plasmodium* Sporozoites Supernatant were generated from cultures containing the mouse hepatoma cells Hepa1-6 and *P. yoelii* sporozoites (mH/Py conditioned media). To detect ISIF activity, fresh hepatoma cells were incubated with mH/Py conditioned media for different periods of time. Cells were then washed and incubated with *P. yoelii* sporozoites. Infection was examined 24 h later by staining the exo-erythrocytic forms of the parasite (EEFs). As controls, we used Hepa1-6 cells preincubated for identical periods of time with fresh medium before addition of *P. yoelii* sporozoites. Pre-treatment of hepatocytes with mH/Py conditioned medium increases the level of infection (FIG. 1a). The greatest enhancement of susceptibility to infection was observed in hepatoma cells that were pre-treated for 1 h with mH/Py conditioned media (FIG. 1a). mH/Py conditioned medium obtained with heat inactivated sporozoites was ineffective (FIG. 1b). Since sporozoites are obtained by dissection of infected mosquito salivary glands, we also tested conditioned media that were obtained from cultures containing hepatoma cells and material of salivary glands from uninfected mosquitoes. Medium conditioned in this way was ineffective (FIG. 1b).

Example 2

Release of ISIF by Wounded Hepatocytes

To investigate the source of ISIF (sporozoites or hepatocytes) and the requirements for its release, Hepa1-6 cells were wounded using mechanical stress. The wounded cells were placed in a tissue culture well and the supernatant was collected after 1 hour. Fresh Hepa 1-6 cells were preincubated with this supernatant before addition of *P. yoelii* sporozoites.

Preincubation with the supernatant resulted in an increase in infection similar to that observed with mH/Py conditioned medium (FIG. 1c). This finding indicates that ISIF is not derived from sporozoites but released from hepatocyte as a consequence of wounding.

Example 3

ISIF is Hepatocyte Growth Factor (HGF)

Figure 2:
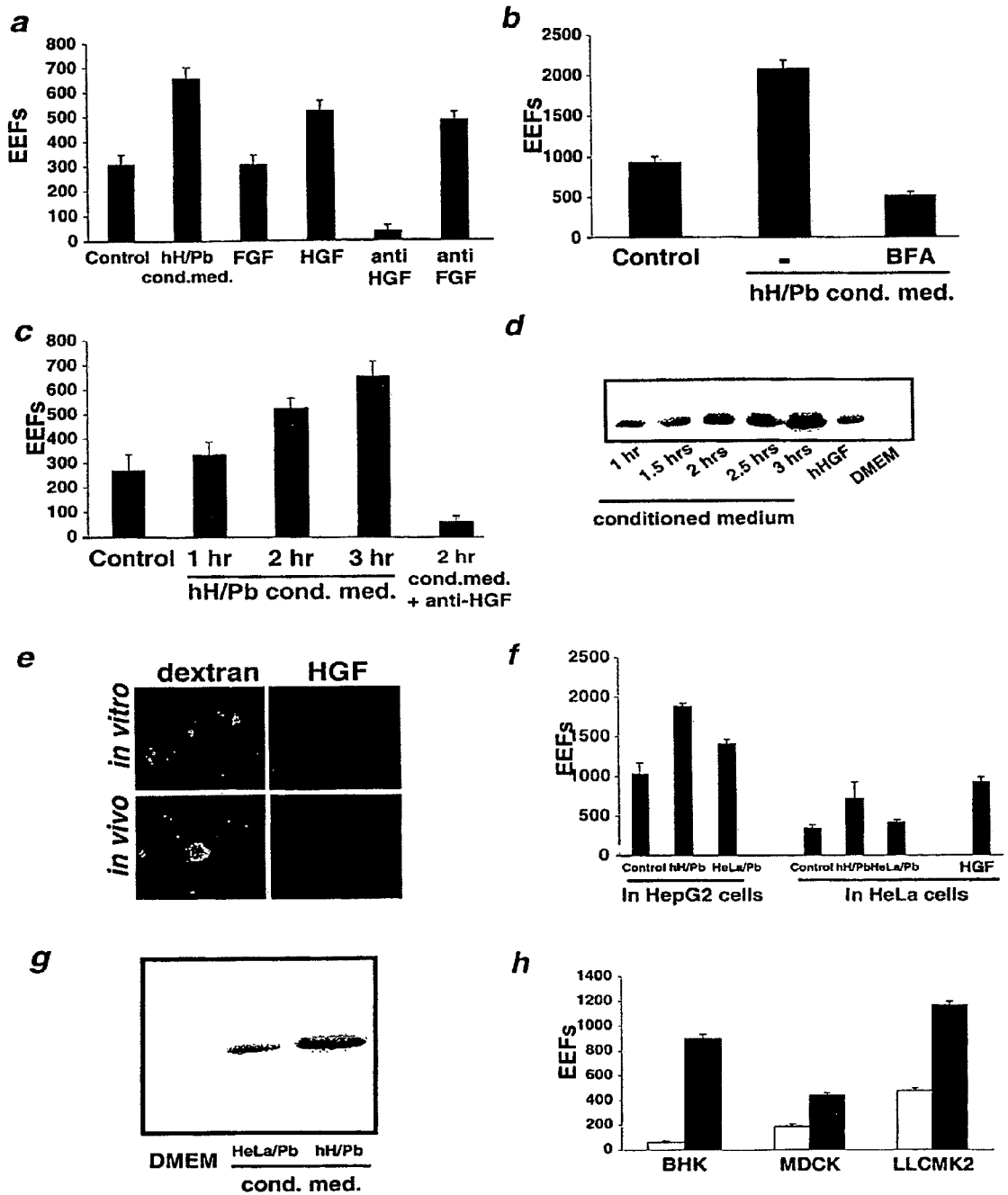
FIG. 2 shows that HGF secreted by sporozoite-traversed host cells is required for infection.

To test whether ISIF activity was mediated by known growth factor, two well-characterized growth factors known to be released after injury were tested: basic fibroblast growth factor (bFGF) and hepatocyte growth factor (HGF). HepG2 cells were pre-incubated with human HGF or bFGF before addition of P. berghei sporozoites. As positive and negative controls, cells were incubated with hH/Pb conditioned medium or fresh medium, respectively. HGF increased infection to a greater extent than the hH/Pb conditioned medium (FIG. 2a). bFGF was ineffective. To determine whether the ISIF in hH/Pb conditioned medium was HGF, a neutralizing monoclonal anti-HGF antibody was added to this medium, before incubation with new HepG2 cells and sporozoites. The antibody not only abolished the effect of the hH/Pb conditioned medium but also decreased infection below the basal level that is observed in control cultures (FIG. 2a). Addition of monoclonal anti-bFGF antibody had no effect (FIG. 2a). These results show that the ISIF in conditioned media is HGF, and indicate that HGF release is a prerequisite for sporozoite infection of hepatocytes.

Example 4

ISIF/HGF is Secreted by Hepatocytes After Wounding

HepG2 cells were treated with Brefeldin-A (BFA), an inhibitor of protein transport to the Golgi vesicles that blocks constitutive secretion in eukaryotic cells. BFA treated cells, and untreated control cells, were then washed and incubated with P. berghei sporozoites to generate conditioned medium. The testing of this conditioned media indicated that BFA treatment inhibits ISIF/HGF secretion (FIG. 2b). The effect of BFA was dose-dependent. Supernatants of mechanically wounded HepG2 cells were collected after various time periods of incubation. ISIF/HGF levels, as determined by the infection susceptibility assay (FIG. 2c) and western blot analysis, (FIG. 2d) increased with time. The ISIF activity was abolished by the addition of neutralizing anti-HGF antibodies (FIG. 2c).

Example 5

Correlation of ISIF/HGF Activity with Infection Levels

Although with lower efficiency, P. berghei is able to infect the non-hepatic epithelial cell line, HeLa (FIG. 2e). A series of experiments was performed to compare HepG2 cells and HeLa cells with regard to parasite induced ISIF/HGF production and responsiveness to ISIF/HGF. Conditioned media were generated from cultures of parasites with HepG2 cells (hH/Pb conditioned medium) and with HeLa cells (HeLa/Pb conditioned medium). Both conditioned media contained ISIF/HGF, albeit at different levels. The ISIF activity correlated well with HGF levels as determined by Western blot and ELISA. Like HepG2 cells, HeLa cells were susceptible to ISIF/HGF. HeLa cell infection was enhanced by hH/Pb conditioned medium and HepG2 infection was enhanced by HeLa/Pb conditioned medium. ISIF activity was always greater in hH/Pb conditioned medium than in HeLa/Pb conditioned medium (FIG. 2e). These data indicate that HeLa cells are responsive to ISIF/HGF and that the extend of infection increases with the dose of HGF.

Example 6

HGF Action on Infection is Mediated Through Met

Figure 3:
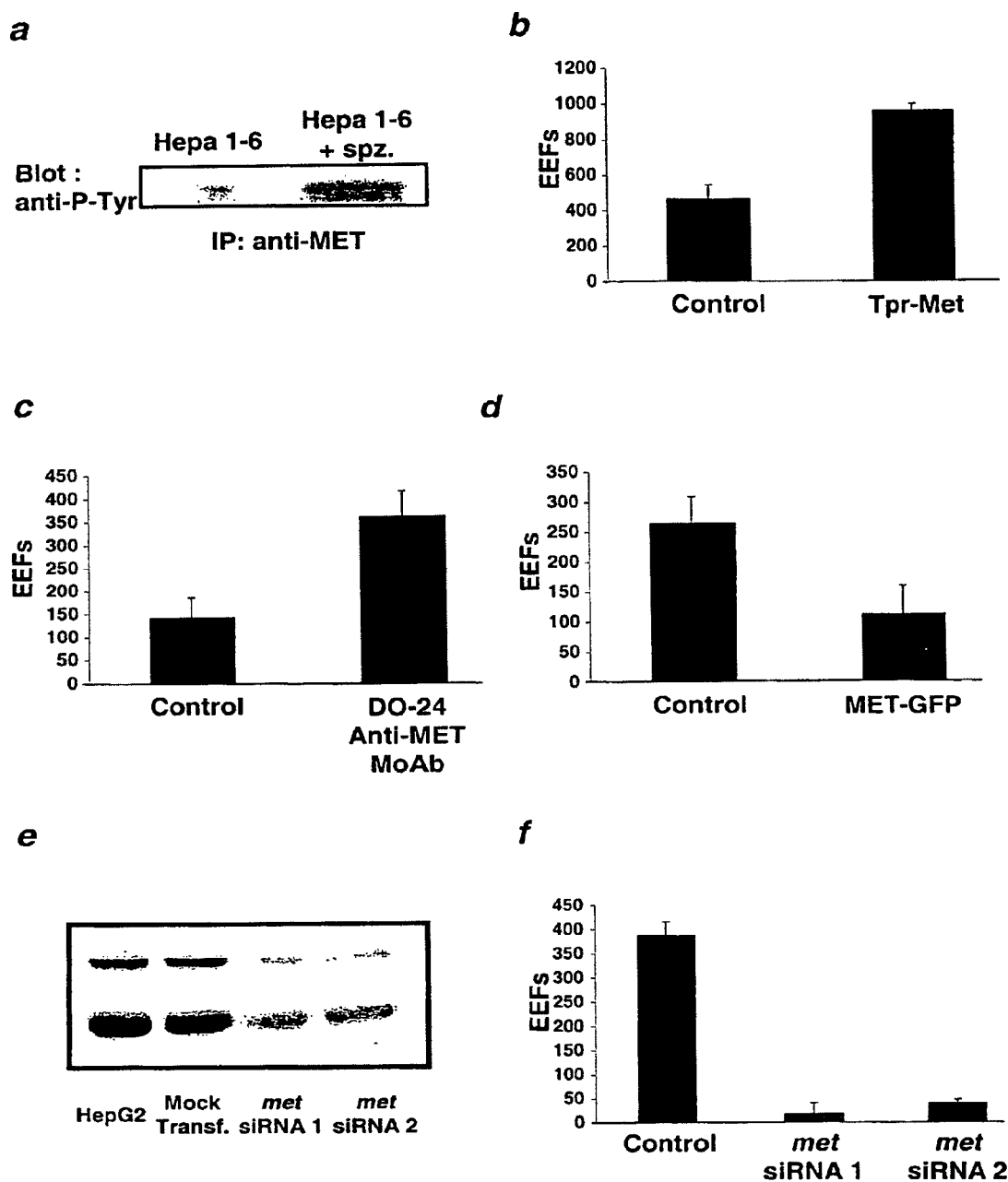
FIG. 3 shows that HGF action on *Plasmodium* infection is mediated through its receptor, MET.

A variety of experimental protocols was used to show that HGF acted via its receptor Met. First, incubation of Hepa1-6 cells with P. berghei sporozoites for 1 h resulted in activation of Met kinase, as demonstrated by tyrosine phosphorylation of the receptor (FIG. 3a). Second, the infection with P. berghei was enhanced in HepG2 cells that were transfected with a constitutively activated MET tyrosine kinase (tpr-Met)[14] (FIG. 3b), as well as in HepG2 cells that were treated with an agonistic monoclonal antibody directed against the extracellular domain of MET[15] (FIG. 3c). These results show that activation of MET enhances the susceptibility of hepatocytes to infection by sporozoites. In addition, since in tpr-Met the tpr sequences replace the extracellular domain of Met, it rules out the possibility that *Plasmodium* sporozoites could use Met as receptor to enter hepatocytes, as occurs in *Listeria* infection.

Two protocols were used to down modulate MET. First, HepG2 were transfected with a chimeric construct containing the extracellular and transmembrane domains of met fused to gfp sequences. The product of this construct is expressed at the plasma membrane, and binds HGF but it is unable to transduce signals into the cell since it lacks the kinase domain and the tyrosines acting as docking sites for intracellular transducers; This chimera behaves as a dominant interfering protein since it dimerizes with endogenous MET, preventing its activation. With a transfection efficiency of 54.3±2.1%, P. berghei sporozoite infection was reduced by about 60% in the total cell population (FIG. 3d). Individual cells that were transfected as indicated by GFP expression, were completely resistant to infection. Analogous experiments with a dominant-interfering construct for an FGF receptor did not affect the susceptibility of HepG2 to P. berghei infection. In a second approach, MET was down modulated using interference RNA. Two independent populations of HepG2 cells were transfected with specific met oligos that caused a reduction of MET expression, as detected by western blot (FIG. 3e). The infection rate of these cells was decreased by 90% as compared to mock transfected cells (FIG. 3f). The results demonstrate that HGF signalling through its receptor MET is a prerequisite for the infection of hepatocytes with *Plasmodium* sporozoites.

Example 7

In Vivo Relevance of HGF/MET Role During a Malaria Infection

Figure 4:
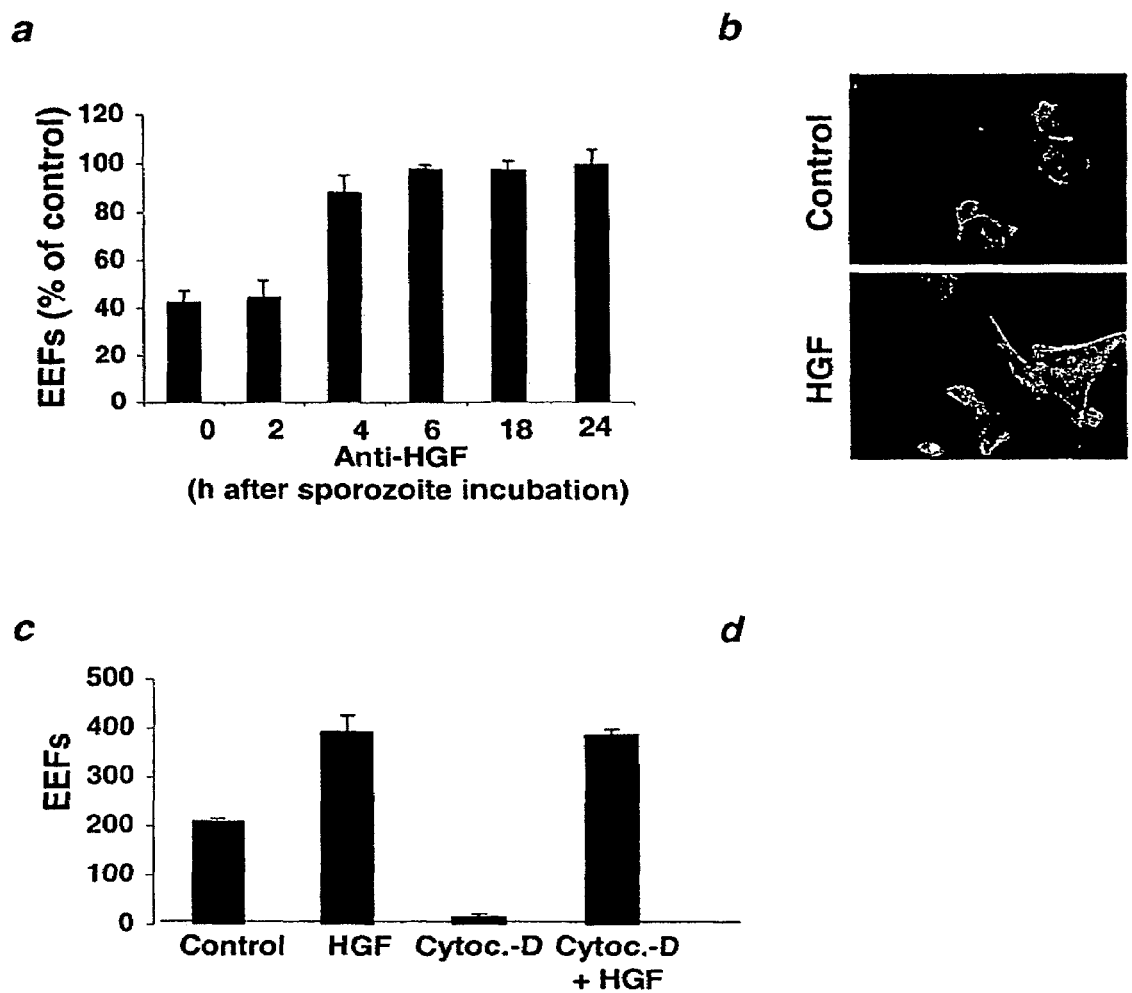
FIG. 4 shows that HGF is expressed by *Plasmodium*-traversed cells in vitro and in vivo and its signaling through MET is essential for malaria infection

Primary hepatocytes were obtained by liver perfusion. Medium conditioned by these cells had a similar ISIF activity as the media that were conditioned by the hepatocyte cell lines (FIG. 4a). A specific HGF receptor inhibitor, K252a, abolished ISIF activity (FIG. 4a). Cells that have been traversed by sporozoites can be detected using a cell-impermeant fluorescent tracer macromolecule that only penetrates into wounded cells. P. yoelii sporozoites were incubated with Hepa1-6 cells in the presence of fluorescent-labelled dextran before staining for HGF. To detect cells traversed by sporozoites in vivo, a standard assay for detection of cell wounding in mice was used. Liver histological sections were obtained and stained for HGF. Both in vitro and in vivo, dextran negative cells did not express HGF, while most dextran positive cells were also positive for HGF staining (FIG. 4b). The results show that hepatocytes traversed by sporozoites during liver infection express HGF, probably as a result of the stress induced by wounding, and that HGF signalling through its receptor MET is required for infection. To prove that MET signalling is required during hepatocyte infection during a malaria natural infection, a group of 3 mice were injected with a lentivirus expressing a dominant interfering protein for MET (MET-GFP, example 7). As control, a group of 3 mice was injected with a similar virus but expressing only GFP. Two days later, mice from both groups were challenged with 300,000 Plasmodium sporozoites. And parasitemias checked 2 or 3 days later. Section of each liver were obtained to determine the level of viral infection (FIG. 4c). The results show that expression of MET-GFP in the liver is required for a natural infection (FIG. 4d).

Example 8

Genistein Effect on Hepatic Infection with
Plasmodium berghei Sporozoites In Vitro HepG2 cells were maintained in DMEM 10% FCS, 1 mM glutamine. P. berghei sporozoites were obtained from dissection of infected Anopheles stephensi mosquito salivary glands. P. berghei sporozoites (5×104) were added to monolayers of $2 \times 10^5$ HepG2 cells (in the presence or not of Genistein) for 24 h before fixation and staining with anti-EEF mAb (2E6), followed by anti-mouse IgG-FITC antibodies. Infection was quantified by counting the number of EEFs per coverslip. The results are shown in FIG. 5. The results show the number of infected cells. Genistein at 25 µM already shows a reduction of approximately 75% in infection.

Example 9

Genistein Effect on Hepatic Infection with
Plasmodium berghei Sporozoites In Vivo Again, P. berghei sporozoites were obtained from dissection of infected Anopheles stephensi mosquito salivary glands. P. berghei sporozoites ($5 \times 10^4$) were injected intravenously into two groups of 5 mice. One of the groups was injected 6 hrs before with 4 mg of genistein in DMSO while the other group was injected with DMSO alone (Control). Liver infection was quantified 42 hrs later by Real-Time RT-PCR with parasite-specific primers. The reduction in infection was approximately 80%.

I. Antimalarial Drugs in Current Use

As previously described, the antimalarial agent of the invention can optionally contain antimalarial drugs, currently in use, in combination with the inhibitor of HGF activity. Following are examples of antimalarial drugs that can be combined with one or more inhibitor of HGF activity.

Although remedies against malaria have long been known to occur in the flowering plant ginghao (Artemisia annua) and in Cinchona bark, today there are only a limited number of drugs available to treat or prevent the disease. The antimalarial drugs in current use are described in a recent review article [Ridley, Nature 415:686-693, (2002)] and in a book edited by P. Rosenthal [Antimalarial chemotherapy. Mechanisms of action, resistance, and new directions in drug discovery, Humana, Totowa, New jersey, (2001)]. The most extensively studied antimalarials are quinolines, antifolate drugs, artemisinins, electron transfer inhibitors such as atoquavone, and antibiotics such as tetracyclines. To counteract the development of resistance some drugs are used in fixed combinations, and several new drug combinations are currently under investigation.

A. Quinolines

A powder produced from the bark of the cinchona tree has long been used to treat fevers in South America. Cinchona powder was introduced into Europe in the $17^{th}$ century and the anti-febrile component, quinine, was isolated by Pelletier and Caventou in 1820. Quinine is currently used for the treatment of severe malaria, multidrug resistant malaria and malaria during the first trimester of pregnancy. Quinidine, the dextrorotary diastereoisomer of quinine, is more active than quinine, but is also more cardiotoxic and more expensive. Because of its wide availability as an anti-arrhythmic agent, parenteral quinidine is used in the US for the treatment of severe malaria. Quinine and quinidine may cause hypotension when given as intravenous bolus injection and also hypoglycemia, which is a particular problem in pregnant women. Based on the quinine structure a large number of related compounds have been synthesized with the aim of identifying more effective and safer anti-malaria drugs. Chloroquine was first synthesized in Germany in 1934 and independently identified as the most promising lead amongst a large series of 4-aminoquinolines that were synthesized in the US during World War II. Chloroquine, known under various Trade names such as Nivaquine, Malarquine, and Aralen, has been the mainstay of P. falciparum chemotherapy for decades. It is cheap, safe when used at the correct dose, highly effective and practicable for outpatient use. Chloroquine is usually well tolerated, although it may induce pruritus, particularly in dark skinned patients, nausea, and rarely neuropsychiatric symptoms or cerebellar dysfunction. Chloroquine may be given by intramuscular or subcutaneous administration, or by intravenous infusion. Resistance against chloroquine has developed slowly, but is now extensive, not only in South East Asia, but also in many areas of Africa. It is currently used for the treatment of non falciparum infections and for the treatment and prophylaxis of P. falciparum malaria in areas in which resistance has not yet emerged.

Chloroquine is a 4-aminoquinoline. A large series of 4-aminoquinolines was synthesized with the aim of identifying novel drugs that are active against chloroquine resistant plasmodium strains. This effort led to the discovery of Amodiaquine (Camoquine) which is currently used for treatment of chloroquine resistant malaria. However, its use is limited by the fact that it exhibits some crossresistance with chloroquine and by adverse effects such as hepatitis and agranulocytosis, when used for prophylaxis. Despite extensive efforts over the last thirty years scientists have failed to produce a cheap and effective 4-aminoquinoline alternative to chloroquine [reviewed by O'Neill et al., Pharmacol. Ther. 77:29-58, (1998)].

In the 1960s two antimalarials, mefloquine and halofantrine, emerged from tests of quinine related structures at the Walter Reed Institute of Medical Research in the US. Mefloquine developed under the Trade name Lariam by Hoffmann La Roche was first applied for prophylaxis in 1985 and has since been used for prevention in 14.5 million people and for treatment in 1.6 million people. It is currently used for the treatment and prophylaxis in areas with chlorquine resistance. Mefloquine has an elimination half life of two to three weeks. A course of treatment comprises two or three doses and adverse effects include gastrointestinal disturbances and neuropsychiatric effects. Like mefloquin, the closely related halofantrine is expensive. As its absorption varies from patient to patient, an intravenous formulation has been developed. Halofantrine is used for the treatment of malaria suspected to be caused by chloroquine resistant *P. falciparum*. Its use is limited by the risk of fatal cardiotoxicity.

Primaquine, an 8-aminoquinoline was developed as a follow up of the finding by Paul Ehrlich in 1891 that methylene blue had weak antiplasmodial activity. From a large series of methoxy and 8-aminoquinoline derivatives pamaquine was first identified as a lead and introduced into medicine in 1926. Pentaquine, isopentaquine, and primaquine emerged from the search for less toxic, more effective compounds of this class. Primaquine was extensively tested during the Korean war and is now used for specific indications. Although related in structure primaquine differs from chloroquine in its mode of action. Unlike other quinoline antimalarials, primaquine acts against hepatic stages of *P. falciparum* and destroys late hepatic stages and latent forms of *P. vivax* and *P. ovale*. The latter activity is unique amongst currently used antimalarials and makes primaquine the drug of choice for the prevention of relapses of malaria, which may occur as late as 40 weeks after a primary attack by *P. vivax* or *P. ovale*. Although primaquine acts against erythrocytic forms of *P. vivax* and *P. ovale*, it does not suppress the primary attack by these parasites. Contrary to the erythrocytic forms of *P. vivax* and *P. ovale*, those of *P. falciparum* are not susceptible to primaquine. Therefore, primaquine is not used for the treatment of malaria caused by *P. falciparum*. Primaquine has a very short half life and must be administered daily. Gastrointestinal adverse effects are usually mild, but more serious oxidant hemolysis can occur, in particular in patients with glucose-6-phosphate dehydrogenase deficiency. The related compound tafenoquine is eliminated much more slowly with a terminal half life of about 14 days. This novel compound may have a larger therapeutic index than primaquine, but its therapeutic role has yet to be established.

B. Artemisinis

Artemisinin is the active ingredient of the Chinese flowering plant ginghao (Artemisia annua) that has been used by Chinese herbalists for the last already 2000 years ago. In the 1960s an ether extract of ginghao, ginghao-su was found to be effective against mouse malaria. The active ingredient was isolated by Chinese scientists in 1972. A water-based artesunate formulation was manufactured in China and used safely for the treatment of more than one million malaria patients. In the US Klayman discovered an Artemisia species, sweet wormwood, and developed an oil-based extract that was tested for the treatment of severe malaria. Because of neurotoxic effect in animals the oil-based formulation was not approved in the Western world. However with the emergence of resistance to quinoline based antimalarials the interest in artemisinins has increased and several semisynthetic derivatives have been produced. Besides artemisinin, which is obtained by extraction from Artemisia annua, several semisynthetic derivatives are in current use. They include artemether, arteether, artesunate and dihydroartemisinin. The latter compound is the metabolite of all other artemisinin-based drugs and the main active agent in the body. Artemisinins have a broad spectrum of activity against all parasite phases within erythrocytes, in particular younger ring forms. Artemisinins decrease parasitemia more rapidly than any other antimalarial drug and suppress gametocyte transmission. The disadvantage of the semisynthetic artemisinin derivatives is that they are more expensive than the parent drug. The short half life of artemisinin derivatives and of its active metabolite dihydroartemisinin requires treatment over a period of 5-7 days, when these compound are used alone. Artemether was initially used for the treatment of severe malaria. However, the intramuscular application of this drug proved not to be better than the intravenous application of quinine. Artemisinin and its derivatives are currently used in combinations with other antimalarials for the treatment of uncomplicated malaria.

C. Mode of Action of Quinolines and Artemisinins

Understanding the molecular mechanism underlying the action of known antimalarial drugs and the resistance that Plasmodia develop against these drugs is important for future drug development. Quinolines and artemisinins are concentrated in the lysosomal food vacuole where they appear to exert their antimalarial activity through interactions with heme. Heme is generated by the degradation of hemoglobin that is abundant in the host's erythrocytes. The ferrous heme (FeII) is oxidized to haematin (FeIII) and sequestered in the cytoplasm as an inert pigment called haemozoin. Haemozoin comprises a structured lattice of aggregated heme dimers. The sequestration of heme protects the parasite against lipid peroxidation or other toxic effects of free heme. The primary target of quinolines are older trophozoites which produce large amounts of ferrous heme in their food vacuoles. Chloroquine and other antimalarial quinolines are thought to inhibit the dimerization of ferrous heme or to prevent its disposal from the food vacuole to the cytoplasm where haemozoin is formed. The anti-malarial action of Artemisinins is also dependent on heme. These drugs are thought to kill parasites via free radicals that are generated as a result of the oxidative cleavage of their peroxide bonds in the presence of ferrous heme. However, the exact mode of action of quinoline antimalarials [Sullivan et al., J. Biol Chem 273:31103-31107, (1998)] and of artemisinins [Olliaro et al., Trends in Parasitology 17:122-126, (2001)] remain to be elucidated.

Resistance of *P. falciparum* to chloroquine and probably other quinolines appears to be due to reduced drug transport into the food vacuole. The defect in drug transport may result from mutations in a putative chloroquine resistance transporter gene (PFCRT) and a P-glycoprotein encoding gene (Pfmdr1). Although artemisinin transport appears to be affected by mutations in the Pfmdr1 gene, no clinical resistance to artemisinin and its derivatives has yet been observed.

D. Antifolates

Besides chloroquine the most important antimalarial drugs are compounds designed to inhibit the synthesis of folate cofactors that are essential for nucleotide synthesis and are involved in amino acid metabolism. The most commonly used antifolate are the 2,4-diaminopyrimidine, pyrimethamine, chloroguamide (proguanil, Paludrine), and the sulphur drugs sulfadoxine, sulfalene or dapsone. Pyrimethamine inhibits dihydrofolate reductase (DHFR) which occurs as a fusion protein with thymidylate synthetase (TS) in plasmodium. The sulfonamide sulfadoxine inhibits dihydroopteroate synthase (DHPS), another enzyme in the folate pathway. The success of antifolate therapy against *P. falciparum* has been attributed to host-parasite differences in drug binding to the corresponding enzymes involved in folate cofactor synthesis. Pyrimethamine has higher affinity for Plasmodium DHFR-TS than for human DHFR. However, other DHFR-TS inhibitors also are selectively toxic to parasites without binding more strongly to the plasmodial enzyme. The increased susceptibility of parasites to antifolates as compared to mammalian cells appears to be at least in part due to differences in the regulation of DHFR translation between malaria parasites and human hosts [Zhang and Rathod, Science 296:545-7, (2002)].

When anti-folate drugs are used alone, resistance to their effect develops rapidly as a result of mutations in the target enzymes, dihydrofolate reductase (DHFR) in the case of pyrimethamine, and dihydroopteroate (DHPS) in the case of sulfadoxine and related sulphur drugs. Therefore antifolates are used in combinations. Pyrimethamine is formulated in fixed combinations with other antifolate compounds such a sulfadoxine, sulfalene or dapson. A fixed combination of pyrimethamine and sulfadoxin known under the Trade name Fansidar represents the most important antifolate therapy of malaria. Sulfadoxine/pyrimethamine or sulfalene/pyrimethamine are used for the treatment of severe *Plasmodium falciparum* infection thought to be chloroquine resistant. The combinations proved to be very useful for intermittent treatment during pregnancy. Occasional hypersensitivity to the sulphur component may cause a painful blistering of the skin. This adverse effect prevents the prophylactic use of sulfadoxin/pyrimethamine. The combination of two compounds acting independently from each other on two different enzymes in the folate pathway was designed to reduce the risk of resistance development. However, unfortunately, unfortunately strains of *P. falciparum* did emerge as a result of the widespread use combination.

More recently antifolates have also been combined in fixed combination with drugs that act against malaria parasites by mechanisms not related to folate synthesis. Atoquavone, a drug originally developed to combat Pneumocystis lung infections in AIDS patients, proved to be effective against malaria, presumably by interfering with electron transport in mitochondria. To counteract rapid development of resistance, atoquavone was combined with chloroguamide (proguanil, Paludrine). The antimalarial activity of proguanil is due to its cyclic triazine metabolite cycloguanil which selectively inhibits the plasmodial, bifunctional dihydrofolate reductase-thymidylate synthetase (DHFR-TS). The atoquavone-proguanil combination marketed under the Trademane Malarone by GlaxoSmithkline Inc. is a safe and effective new drug against malaria. However, due to its complex synthesis atoquavone is expensive. The manufacturer has initiated a drug donation program for Africa but the number of treatments donated is likely to be insufficient for its first-line use.

E. Antibiotics

Plasmodium and several other parasites possess a plastid organelle known as the apicoplast, which contains a 35 kb of circular DNA. The plastid integrates elements which resemble prokaryotic transcription and translation systems. This system is susceptible to compounds known to inhibit bacterial protein synthesis such as tetracycline, doxycycline and clindamycin. Because of their slow mode of action these antibiotics are mainly used in combinations with other, fast acting drugs. The use of tetracycline and of doxycycline is limited to patients older than 8 years of age and contraindicated in pregnant and breast feeding women. Both antibiotics are used in combination with quinine. Clindamycin (7-chloro-linomycin), a semisynthetic derivative of linomycin, was introduced in the 1960s as an antibiotic. Clindamycin is safe in children and pregnant women. Several generic formulations of clindamycin are available. A three day treatment course costs more than sulfadoxine/pyrimethamine but less than atovaquone-proguanil or halofantrine. Clindamycin has been used for monotherapy of malaria in several trials, but it is most useful in combinations with a fast acting drug [Lell and Kremsner, Antimicrobial Agents and Chemotherapy 46:3215-2320, (2002)].

F. Treatments that Inhibit the Hepatic Development of Malaria Parasites

Amongst the antimalarial drugs in current use there are only a few which act against the development of plasmodium in liver cells. These include primaquine and the antifolate combination pyrimethamine/sulfadoxin. While the mechanism of action of primaquine against hepatic forms of plasmodium is not known, the antifolate combination presumably inhibits the synthesis of plasmodial DNA that is required for sporozoites multiplication. The present invention provides a novel drug target and drug target candidates that interfere with the hepatic development of plasmodium.

II. Current Efforts in Antimalaria Drug Development

A. Drug Resistance Reverters

The major problem of antimalarials is the development of drug resistant Plasmodium strains. Resistance to drugs may be counteracted by combining them with compounds that revert resistance. Resistance of *P. falciparum* to chloroquine can be reduced in vitro by a large variety of compounds [Singh and Puri, Acta tropica 77:185-193, (2000)]. However, in a mouse model only cyproheptadine proved to be curative against a chloroquine resistant line of *P. yoelii* nigeriensis while other such verapamil and the anti-histamine chlorpheniramine showed moderate activity. Chlorpheniramine is frequently used to treat pruritus caused by chloroquine. In clinical studies the chloroquine/chlorpheniramine combination produced a higher cure rate than chloroquine alone [Sowumi et al., Tropical Mecicine and International Health 3:177-185, (1998)], while in a previous study there was no clinical benefit of the combination of chloroquine with desipramine [Warsame et al. Transactions of the Royal Society of Tropical Medicine Hygiene 86:235-236, (1992)]. Antisense oligonucleotides designed to reduce the expression of a protein involved in drug transport are described in U.S. Pat. No. 6,440,660 B1, published in Aug. 27, 2002.

B. Novel Antimalaria Drug Combinations

The most important strategy to combat resistance is the use of combinations of drugs. As mentioned already above, this strategy has been used in the past through the utilization of fixed combinations such as pyrimethamine and sulfodoxine (Fansidar) or atoquavone and proguanil (Malarone). More recently a variety of novel strategies have been implemented and several other are under investigation [for reviews see a recent publication of the World Health Organization (WHO/CDS/RBM/2001.35)]. Quinoline compounds such as chloroquine, amodaquine, mefloquine and quinine are combined with the antifolate combination sulfadoxine/pyrimethamine. The combination of mefloquine and sufadoxine/pyrimethamine (Fansimef, Roche) was developed on the basis of the observation that these compounds have additive antimalarial activities. However, unexpectedly, the use of this combination as a first line treatment of uncomplicated malaria led to the rapid development of resistance against mefloquine. Therefore the combination is not recommended neither for prophylaxis nor for treatment. Artemisinins are combined with longer half life drugs to reduce treatment time and increase compliance. The rapid clearance of parasites with artemisinins is thought to reduce the chance of development of resistance against the partner drugs. Artemisinin-based combinations include artesunate plus chloroquine, or amodaquine, or mefloquine, or sulfadoxine/pyrimethamine and the combination of artemether with lumefantrine. The latter combination known under the Trade names Coartem and Riamet (Novartis) is available as a fixed combination and represents the most promising combination treatment currently available. This combination has recently been approved by the regulatory authorities. Combinations under investigation include various piperaquine-dihydroartesmisinin-trimethoprim (Artecom), Artecom plus primaquine (CV8), artesunate plus pyronaridine, naphtoquine plus dihydroartemisinin and chloroguanil-dapsone plus artesinate (CDA or Lapdap plus). The antibiotics tetracycline and doxycycline are frequently used in combinations with quinine, and clindamycin is combined with quinine, chloroquine, and more recently with fosmidomycin, a novel antimalaria drug that inhibits 1-deoxy-D-xylulose 5-phosphate (DOXP) reductoisomerase, a key enzyme of the nonmevalonate pathway of isoprenoid biosynthesis.

C. Novel Antimalaria Drugs

Antimalarial drug development can now be expected to advance more quickly than in the past, as the mechanisms underlying drug actions and drug resistance are elucidated and as the understanding of biochemical pathways that are utilized by plasmodia increases. An overview on metabolic pathways in plasmodium is available on the internet (http://sites.huji.ac.il/malaria/). The learning process has been accelerated by the implementation of the plasmodial genome project, the development of improved transfection technologies, and the application of RNA interference technology. Novel approaches to antimalarial drug development are reviewed in recent publications [Winstanley, Parasitology Today 16:146-153, (2000); Antimalarial chemotherapy. Mechanisms of action, resistance, and new directions in drug discovery, Humana, Totowa, N.J., edited by P. Rosenthal, (2001); Ridley, Nature 415:686-693 (2002); Robert and McConkey, Molecular & Biochemical Parasitology 119:273-278 (2002)]). A brief description of these efforts is provided in the following section for the purpose of contrasting these efforts with the strategy that is the subject of the present invention.

The current approaches to malaria therapy may be divided into three categories: improved versions of known drugs, drugs that are directed against newly identified targets, and drugs with unknown or poorly defined targets.

1) Improved Versions of Known Drugs.

Chloroquine remains an attractive lead to novel drug development. Examples of new lead compounds include short chain chloroquine analogues (bisquionlines), analogues of amodiaquine that lack the ability to form a toxic metabolite, and pyronaridine, a 4-aminoquinoline developed originally in China. High throughput screening of large compound libraries has been employed to identify novel structures that bind heme in an analogous way to the binding of quinolines. Artemisinine related trioxanes are described in U.S. Pat. No. 6,136,847, published in Oct. 24, 2000. Novel drug candidates also include biguanides that are directed against DHFR, the target of pyrimethamine and other inhibitors of purine and pyrimidine metabolism in plasmodium (U.S. Pat. No. 5,663,155, published in Sep. 2, 1997). Novel inhibitors for cytochrome c reductase, the target of atovaquone, include β-methoxyacrylates.

2. Drugs that are Directed Against Newly Identified Targets.

2.1. Protease inhibitors. Protease inhibitors for treatment of infections by metazoan parasites are described in U.S. Pat. No. 5,739,170, published in Apr. 14, 1998 and in U.S. Pat. No. 6,194,421 B1, published in Feb. 27, 2001.

2.1.2. Proteases involved in hemoglobin degradation. The erythrocytic forms of plasmodium degrade up to 80% of the hemoglobin of the host cell in the food vacuole. Hemoglobin is broken down within the food vacuole into peptides that are then exported into the cytoplasm for final degradation into amino acids. Enzymes involved in hemoglobin degradation include aspartic proteases (plasmepsins), the cysteine protease falcipain, a metallopeptidase and several other peptidases. The best known hemoglobin degrading proteases are aspartic proteases [Coombs et al., Trends in Parasitology 17:532-7, (2001)]. Drugs have previously been developed which inhibit the catalytic activity of the aspartatic protease of human immunodeficiency virus (HIV) and leads have been identified which inhibit human aspartic proteases such as renin, and aspartatic proteases from various pathogenic microorganisms such as *Aspergillus* and *Candida*. A homology search of the plasmodium genome has revealed eight plasmepsins in addition to the two previously known plasmepsins I and II. Inhibitors of plasmodial plasmepsins may be found in the large collections of compounds that have been synthesized for screening drugs directed against human aspartic proteases. Homology modeling revealed inhibitors of the cysteine protease falcipain-2 (vinyl sulfones, isopuinolones) which inhibit the in vitro growth of malaria parasites [Sabnis et al., J. Biomol. Struct. Dyn. 19, 765-74, (2002)]. The challenge is to discover inhibitors that are active against plasmodial enzymes but not, or to a much lesser extent, against the homologous, human proteases.

2.1.3. Proteases involved in erythrocyte invasion. The entry of merozoites into erythrocytes requires the proteolytic cleavage of several proteins on the parasite and the erythrocyte surface. Two proteases expressed by merozoites, *P. falciparum* subtilisin-like protease-1 and -2 (PfSUB-1 and PfSUB-2), have been studied. These and several others are potential drug targets [Blackman, Curr. Drug Targets 1:59-83, (2000)].

2.2. Fatty acid synthesis. Fatty acids synthesis occurs as iterative elongations of acyl chains utilizing the 2-carbon donor malonyl coenzyme A (CoA). In bacteria the pathway (known as the type II pathway) involves several fatty acid synthases (FAS). In animals the pathway (known as type I pathway) is catalyzed by a single large multifunctional protein. The type II pathway for de novo fatty acid synthesis occurs not only in bacteria but also in plants and in the apicoplasts of certain parasites including plasmodium. The plasmodial type II pathway involves the acyl carrier protein (ACP), β-ketoacyl-ACP synthases III (FabH) and I/II (FabB/F), and enoyl-ACP reductase (FabI). The antibiotics triclosan, and thiolactomycin and derivatives thereof are lead compounds in the search for new antimalarial drugs that inhibit fatty acid synthesis [Waller et al., Antimicrobial Agents and chemotherapy 47:297-301, (2003); Prigge et al., Biochemistry 42:1160-69, (2003)].

2.3. The non-mevalonate pathway of isoprenoid synthesis. While isoprenoids are synthesized in humans via the mevalonate pathway, in plasmodium they are synthesized by a nonmevalonate pathway, also called the MEP pathway. This pathway is known to operate in certain bacteria and plants. In plasmodium it involves enzymes that are encoded by the circular DNA in the apicoplast. The 1-deoxy-D-xylulose 5-phosphate [DOXP] reductoisomerase, a key enzyme of the nonmevalonate pathway is inhibited by fosmidomycin. This antibiotic was originally isolated from *Streptomyces lavendulae*. Fosmidomycin possesses potent antimalarial activity in vitro and in murine malaria. Initial clinical trials show that the drug is well tolerated. However, unfortunately, the drug leads to rapid development of resistance. Therefore it must be used in combinations with other drugs. Preclinical studies suggest that the combination of fosmidomycin with lincomycin and clindamycin may be useful.

2.4. Protein prenyltransferases. A variety of proteins including small G-proteins, such as Ras, Rac, Rap, Rho, Rab, heterotrimeric G protein γ-subunits, nuclear lamins, protein kinases, and protein-tyrosine phosphatases are post-translationally prenylated near the carboxyl terminus with farnesyl (C15) or geranylgeranyl (C20) groups. The attachment of the farnesyl or geranylgeranyl groups are catalyzed by prenyltransferases. Inhibitors of these enzymes are extensively studied anticancer drug candidates. Two prenyltransferases, PFT and PGGT-I have been identified in *plasmodium falciparum*. Several peptidomimetics and the monoterpene, limonene, inhibit prenylation and parasite growth [Chakrabarti et al., J. Biol. Chem. 277:42066-73, (2002)]. Farnesyltransferase inhibitors (phosphosequiterpenes) are described in U.S. Pat. No. 6,429,203, published in Aug. 2, 2002).

2.5. Lactate dehydrogenase (LDH). Plasmodial LDH (PLDH) is essential for the anaerobic generation of ATP by the sexual and asexual stages of plasmodium. Different isomers of PLDH are found in different plasmodium species. Their detection is used as a diagnostic test and for monitoring the antimalarial efficacy of drugs. Due to structural differences to human LDH, pLDH is considered a promising drug target [Dunn et al., Nat. Struct. Biol. 3:912-5, (1996)].

2.6. Phospholipid biosynthesis inhibitors. Development and proliferation of the erythrocytic plasmodium requires large amount of phospholipids. Phosphatidylcholine (PC), the major phospholipid present in infected erythrocytes is mainly synthesized from plasma-derived choline by enzymes of the parasite. A large number of choline like compounds have been synthesized and some have antimalarial activity. A lead compound, G25 and its analog, VB5-T, VB5-T, inhibit the in vitro growth of *P. falciparum* and *P. vivax* at concentration that are not toxic to mammalian cell lines. A very low dose G25 therapy cured monkeys infected with *P. falciparum* and *P. cynomolgi*. These choline based drugs appear to interfere with choline uptake and thus with PC synthesis [Wengelnik et al., Science 295:1311-14, (2002)].

2.7. Glycosylphosphatidylinositol (GPI) synthesis. GPIs are ubiquitous among eukaryotes. They are synthesized in the endoplasmic reticulum (ER) by the sequential addition of sugar residues to phosphatidylinositol (PI) by the action of glycosyltransferases. The maturing GPI is translocated across the membrane from the cytoplasmic to the luminal side of the ER. After completion of synthesis, GPI glycolipids are exported to the cell surface, free or in covalent association with proteins. GPIs are important, inflammation inducing compounds of plasmodium as well as of other parasites. Two GPI anchored protein, the circumsporozoite protein (CS) and the merozoite surface proteins MSP-1 and MSP-2 as well as GPI itself are vaccine candidates. Since there are differences between PGIs of plasmodium and those synthesized by mammals, GPI synthesis in plasmodium is an attractive drug target [Delorenzi et al Infection and Immunity 70:4510-4522, (2002)].

Proof of principle for this approach has been obtained in *Trypanosoma brucei*: a block in GPI synthesis by the disruption of the PIG-B gene makes blood stages of *T. brucei* nonviable.

2.8. Protein kinases. Plasmodial protein kinases can be divided into several groups and families [Kappes et al., Parasitology Today 15:449-454 (1999)]. Most of these kinases show 40 to 60% homology to their mammalian counterparts at the amino acid level. Of particular interest for drug development are the calcium dependent protein kinases (CDPKs) which have been found in plants and some protozoan species but not in mammals and several kinases which have large insertions in the catalytic domain such as PfPK1, PfPK4 and FEST. Pfnek-1 is one example of a potential drug target in this class. It shows homology to the never-in-mitosis/*Aspergillus* (NIMA)/NIMA-like kinase (Nek) family of protein kinases that are involved in eukaryotic cell division. Similar to other *P. falciparum* protein kinases and NIMA/Nek family, Pfnek-1 has large C-terminal extension besides the catalytic domain. One of its substrates is Pfmap-2, an a typical *P. falciparum* MAPK homologue. Bacterially expressed recombinant Pfnek-1 protein can be used in inhibition assays to screen for inhibitors [Dorin et al., Eur J Biochem 268:2600-8, (2001)]. Proteins with homology to known protein tyrosine kinases have not been found in plasmodium, although protein tyrosine phosphorylation has been reported to occur.

2.9. Polyamines. Like all eukaryotes plasmodium contain three polyamines, the diamine putrescine, and its derivatives, spermidine and spermine. The compounds have pleiotropic functions in cell proliferation and differentiation. Stragies for interfering with polyamine functions include inhibition of polyamine synthesis, of polyamine back conversion, and of polyamine transport, or de-regulation of polyamine metabolism by structural analogues. Combinations of polyamine synthesis inhibitors with polyamine structural analogues for the treatment of malaria and of diseases caused by other pathogenic protozoan are under investigation. This approach benefits from the large compound libraries that have been generated in the search for novel anti-cancer drugs

[Muller et al., Trends in Parasitology 17:242-9, (2001)].

2.10. Histone Deacetylatase.

Histones are nuclear proteins involved in the regulation of transcription via the continuous acetylation/deacetylation of specific lysine residues. In *P. falciparum* histones are abundant and at least one histone deacetylase has been identified. Apicidin, a cyclic tetrapeptide isolated from *Fusarium* spp inhibits mammalian cell proliferation and in vitro development of Apicomplexan parasites, including *Plasmodium* species [Darkin-Rattray et al. Proc Natl Acad Sci USA 93:13143-7, (1996)], probably by interfering with the continuous acetylation/deacetylation process. This finding led to the search for parasite selective histone deacetylase inhibitors. Lead compounds include trichostatin A (TSA), sodium n-butyrate, hexamethylene bisacetamide (HBMA), and more recently developed HMBA analogues such as azelaic bishydroxamic acid (ABHA) and the analogues of suberic acid bisdimethylamide [Andrews et al., International Journal For Parasitology 30:761-768, (2000)].

2.11. Shikimate pathway. The shikimate pathway occurs in prokaryotes, fungi and the plastids of plants and algae, but not in vertebrates. The pathway generates chorismate, an essential substrate for the synthesis of p-aminobenzoate (PABA) and folate. It is also required for the synthesis of ubiquinone, aromatic amino acids and almost all other aromatic compounds. Mammals, which do not have the shikimate pathway rely on exogenous folates. Chorismate synthase (CS) was validated as a useful drug target using the recently developed RNA interference technology [Robert and McConkey, Molecular & Biochemical Parasitology 119:273-278 (2002)]). Leads for drugs which inhibit the pathway are already available. The herbicide glyphosate (better known by its Trade names of RoundUp, Zero or Tumbleweed), an inhibitor of 5-enopyruvyl shikimate 3-phosphate synthase, inhibits the growth of plasmodium in vitro.

2.12) Cyclophilins. Cyclophilins occur in all living organisms. Human cyclophilin A (hCyPA) was originally identified as a cytosolic target for the immunosuppressive drug cyclosporin A (CSA). Attempts to suppress immunity of mice with CSA revealed the unexpected fact that CSA inhibits the growth of rodent malaria. CSA and several nonimmunosuppressive CSA analogues have subsequently been shown to have antimalarial activity in vitro. The early erythrocytic, ring stage parasites appear to be particularly susceptible. Amongst one of three cloned, plasmodial cyclophilins, PfCyP19 is the closest homolog of human CypA. Like other cyclophilins PfCyP19 has peptidylprolyly cis/trans isomerase (PPlase or rotamase) activity. It binds CSA with high affinity. Its ability to inhibit parasite growth appears not to be related to inhibition of rotamase activity but rather the inhibition of an unidentified target protein by the PfCyP19-CSA complex.

2.13. Transport systems. Parasite invasion of erythrocytes is associated with alterations in its membrane transport systems and with the appearance of new permeation pathways (NPP) that are not found in uninfected erythrocytes [reviewed by Kirk, Physiological Reviews 81:495-537, (2001)]. Parasite and/or red cell derived transporter proteins are located at the vacuolar membrane and at the parasite surface. Some of the transporters at the parasite surface such as ATP/ADP exchanger, V-type H1-ATPase, H1-PPase are typically found on the membranes of intracellular organelles. The Transport proteins are of interest for new approaches to malaria chemotherapy. On the one hand, drugs may be designed which block nutrient uptake by the parasite. On the other hand the transport systems may be exploited as routes for the targeting of cytotoxic agents into the intracellular parasite. Drug target candidates under investigation include A voltage-dependent channel located at the surface of infected erythrocytes that plays a role in nutrient uptake [Desai et al., Nature 406:949-51, (2000)], proteins involved in the uptake of $\delta$-aminolevulinate dehydratase (ALAD) and perhaps of other host enzymes used by plasmodium for heme synthesis [Bonday et al., Nature Medicine 6:898-903, (2000)], and a parasite-encoded hexose transporter that is localized to the parasite plasma membrane within the infected red cells [Woodrow et al., J. Biol. Chem. 274:7272-7, (1999)].

3. Antimalarial Drugs for which the Mechanism of Action is Unclear.

3.1 Tryptanthrins. After its synthesis in 1963 indolo[2,1-b]-quinazoline-6,12-dione (tryptanthrin) was isolated from Isatis tinctoria (woad), an old European and Chinese dye plant and medicinal herb. The compound can be readily synthesized and is produced by Candida lipolytica when grown in media containing an excess of tryptophan and anthranilic acid, hence the name tryptanthrin. Tryptanthrin is active against a variety of microorganisms, in particular intracellular microbes such as mycobacteria, Leishmania donovani, Trypanosoma cruzi, and plasmodia [Bhattacharjee et al, Bioorganic & Medicinal Chemistry 10:1979-1989, (2002); Scovill et al., Antimicrobial Agents And Chemotherapy 46:882-883, (2002)]. The compound is an agonist of the aryl hydrogen receptor, induces cytochrome P4501A1 expression in hepatocytes [Schrenk et al., Biochem. Pharmacol. 54:165-71, (1997)] and inhibits cyclooxygenase-2 as well as 5-lipoxygenase [Danz et al., Planta Med. 68:152-7, (2002)]. The mechanism of action against intracellular microorganisms is not known. A series of derivatives developed for optimal activity against malaria parasites is described in U.S. Pat. No. 6,284,772, published in Sep. 4, 2001.

3.2 Febrifugene. Febrifugine and isofebrifugine was discovered in the late 1940 and early 1950s as an antimalarial agent in extracts from Dichroa febrifuge or Hydrangea umbellate. Although febrifugene exhibits structural similarity with chloroquine [Chang, J. Theor. Biol. 59:497-501, 1976)] its antimalarial action appears not to be related to hemoglobin degradation. The compound increases nitric oxide production, a possible mode of action against plasmodium [Murata et al., Biochemical Pharmacology 58:1593-1601, (19990]. Febrifugene synthesis and its antimalarial activity are described in U.S. Pat. No. 6,420,372B1.

3.3. Hybrid peptides. Peptides consisting of naturally occurring cyclic peptides such as cecropins, attacins, magainins, sacrotoxin, sapecin, bactenecins, alamethidicins, defensins and PGLA2 and toxins such as streptolysin, melittin, barbatolysin, paradaxins and delta hemolysin are described as antimalarial compounds in U.S. Pat. No. 5,714,467, published in Feb. 3, 1998.

III. Anti-Malaria Effects of Cytokines

Interleukin-1 (IL-1) inhibits the hepatic development of *P. falciparum* sporozoites in rhesus monkeys, but only when applied before sporozoites inoculation [Maheshwari, Bull. World Health Organ. 68:138-44, 1990)]. The protective effect of IL-1 may be due to its ability to induce acute phase proteins such as IL-6 [Vreden et al., Eur. J. Immunol. 22:2271-5, (1992)] or c-reactive protein (CRP). CRP binds to sporozoites of *P. falciparum* and *P. yoelii* probably via phosphorylchloine binding sites, and thereby inhibits infection of hepatocytes in vitro and in vivo. Injection of turpentine oil also induces CRP production and protects rats against malaria infection. The protective effect can be transferred with sera from turpentine oil injected rats and this protection is abolished by anti-CRP antibodies [J. Immunol 139:4192, (1987)]. Interferon-$\gamma$ (IFN-$\gamma$) appears to interfere with the development of exoerythrocytic forms (EEFs) of plasmodium within liver cells [J. Immunol 138:4447]. At low doses IFN-$\gamma$ inhibits EEF development within hepatocytes in vitro [J. Immunol 139:2020, (1987)] and in vivo [Ferreira et al., Science 232:881-884, (1986); Masheshwari et al., Inf. Immunity 53:628-630, 1986)]. Five doses of human IFN-$\gamma$ given on days −2, 0, and +2 protected rhesus monkeys against infection with *P. Cynomolgi* sporozoites on day 0. No protection was observed against trophozoite-induced infections [Maheshwari, Bull. World Health Organ. 68:138-44, 1990)]. The use of IFN-$\gamma$ for the treatment of malaria is described in U.S. Pat. No. 5,270,037, published on Dec. 14, 1993 and U.S. Pat. No. 4,915,941, published in Apr. 10, 1990. Tumor necrosis factor (TNF) administration did not protect against infection by *P. vinckei* (Acta Tropica 45:289, (1988)], but prolonged administration via a minipump reduced parasitemia after infection with sporozoites from *P. chabaudi* [J. Immunol. 139:3493, 1987)].

IV. Malaria Vaccines

Another important strategy to combat malaria is vaccination. Induction of protective immunity by immunization with attenuated microorganism or nonpathogenic components has been a major triumph of medicine. Vaccination has virtually eliminated morbidity and mortality from several acute infectious diseases. Unfortunately, vaccination has been less successful in preventing chronic infections such as tuberculosis and malaria. Intensive efforts have been made in the second part of the 20th century to develop vaccines against the three major developmental stages of *P. falciparum* and *P. vivax*. Vaccines against pre-erythrocytic stages aim to prevent the infection from entering the blood of a human host. Vaccines against the asexual blood stage parasites aim to combat these disease-causing stages once the infection has entered the blood. Vaccines against the sexual stages of the parasites in the blood and in the mosquito mid gut aim to prevent the parasites from infecting the mosquito vectors and thereby interrupt the transmission of malaria in human and mosquito populations. Currently, multicomponent vaccines are under development. These vaccines aim to induce humoral and cell mediated immunity directed against multiple antigens that are expressed at different stages of plasmodial development [for a recent example see Kumar et al., Trends in Parasitology 18:129 (2002)]. None of the vaccines tested in the past has proven to be effective.

IV. Targeting Host Components

The targets of vaccines and of most antimalarial drugs are components of the parasite. Many of these targets are involved in host parasite interactions that are essential for the survival and growth of the parasite and/or involved in the pathology that is caused by the infection. A possible alternative to current strategies is to modulate host components known to interact with molecules generated by the parasites. At first sight this strategy seems counterintuitive. Indeed, an important requirement of traditional anti-microbial chemotherapy is not to interfere with functions of the host. However, targeting of host components has the advantage that drug resistance cannot result from alterations of the drug target. Two important classes of antimalarial drugs, the quionlines and the arteminisinis are exceptional in that they target heme, a component of the host. Resistance against quinolines developed very slowly as it required the selection of variants that affect drug transport. Resistance is even less likely to occur if the targeted host component remains outside of the microorganism. In rodent models of malaria the disease can be prevented or ameliorated by blocking host cell proteins on the surfaces of hepatocytes or of erythrocytes, and by a variety of signal transduction inhibitors (see below). These findings have contributed to the understanding of the pathogenesis of the disease and to the design of vaccines, but have not promoted any projects of antimalarial drug development. The present invention relates to a protein that is generated by the host and is required by malaria parasites to establish an infection. This host protein is not enclosed within membranes of the parasite. It is a protein tyrosine kinase known as Met which serves as a receptor for another host protein known as hepatocyte growth factor.

It will also be understood that the method of this invention can be practiced with compounds that change in vivo into the antimalarial agent, as well as compounds that produce metabolites in vivo similar to the metabolites formed form the antimalarial agent.

Combinations of one or more of the antimalarial drugs can be employed in practicing the method of this invention. Thus, for example, the inhibitors of HGF activity can be employed together with other antimalarial drugs such as chloroquine or together with combinations of antimalarial drugs such as Sulfadoxine/pyrimethamine. The antimalarial drug can be employed in the form of the free base or in the form of a pharmaceutically acceptable acid addition salt. Examples of suitable salts are the chlorides, hydrochlorides, sulfates, phosphates, and diphosphates. Other water soluble, non-toxic, inorganic and organic salts can also be employed.

In practicing the method of the invention, the antimalarial agent is administered to a human host by the oral route, since its mode of action is primarily in the liver. For purposes of oral administration the antimalarial agents of the present invention can be prepared in solid forms such as capsules, tablets, pills, powders, troches, and granules or in liquid forms, e.g., emulsions, solutions, suspensions, syrups and elixirs containing inert diluents commonly used in the art, such as water. Other modes of administration can also be employed.

The antimalarial agent is employed in the method of the invention in an amount sufficient to provide an adequate concentration of the agent to prevent or at least inhibit infection by malaria vectors in vivo or to prevent or at least inhibit spread of malaria in vivo. The amount of the agent thus depends upon absorption, distribution, and clearance by the human host. Of course, the effectiveness of the antimalarial agent is dose related. The dosage of the antimalarial agent should be sufficient to produce a minimal detectable effect, but the dosage should be at least 10 times below the established lethal dose. The dosage of the antimalarial agent administered to the host can be varied over wide limits. The agent can be administered in the minimum quantity, which is therapeutically effective, and the dosage can be increased as desired up the maximum dosage tolerated by the patient. The antimalarial agent can be administered as a relatively high loading dose, followed by lower maintenance dose, or the agent can be administered in uniform dosages.

The dosage and the frequency of administration will vary with the antimalarial agent employed in the method of the invention. For example, Genistein can be employed by the oral route in an amount of 5 mg per day to about 5000 mg/day, preferably about 50 mg per day to about 500 mg/day. Generally, the dosage will not exceed about 500 mg per day, and most often not more than about 50 mg per day. The dose of the antimalarial agent is specified in relation to an adult of average size. Thus, it will be understood that the dosage can be adjusted by 20-25% for patients with a lighter or heavier build. Similarly, the dosage for a child can be adjusted using well known dosage calculation formulas.

The amount of the antimalarial drug used in combination with the inhibitor of HGF activity to form the antimalarial agent of the invention generally will not exceed the amount found to be safe and effective for the treatment of malaria. Thus, as an example, primaquine diphosphate can be orally administered in tablets containing 5 mg-7.5 mg of the drug at a rate of 2-3 tablets per day. The dose of primaquine for adults is about 15 mg/day base (26 mg/day salt) orally or about 45 mg/wk base (79 mg/wk salt) orally. For children the dose is about 0.3 mg/kg per day base (0.5 mg/kg per day salt) orally or about 0.9 mg/kg per week base (1.5 mg/kg per week salt) orally.

The effectiveness of the antimalarial agents of the invention in preventing or inhibiting infection of cells is demonstrated using standard in vitro assays. Thus, the inhibitory effect of the antimalarial agent on malaria infection or replication can be demonstrated by adding malaria sporozoites to hepatocyte cultures in the presence or absence of the antimalarial agent and then testing the proliferation of sporozites within hepatocytes by standard methods. The effectiveness of the antimalarial agent in preventing or inhibiting malaria infection or replication can be confirmed in vivo in mammalian models of malaria infection. Malaria required to carry out these assays can be obtained from conventional sources using conventional techniques.

The antimalarial agents and their pharmaceutically acceptable salts can be used in mammalian, including but not limited to human, prophylaxis or therapy in the form of pills, tablets, lozenges, troches, capsules, suppositories, injectable or ingestable solutions and the like.

Appropriate pharmaceutically acceptable carriers, diluents, and adjuvants can be combined with the antimalarial agents described herein in order to prepare the pharmaceutical compositions for use in the treatment of pathological conditions in mammals. The pharmaceutical compositions of this invention contain the active agent together with a solid or liquid pharmaceutically acceptable nontoxic carrier. Such pharmaceutical carriers can be sterile liquids, such as water and oils, including those of petroleum, animal, vegetable, or synthetic origin. Examples of suitable liquids are peanut oil, soybean oil, mineral oil, sesame oil and the like. Water is a preferred carrier when the pharmaceutical composition is administered intravenously. Physiological saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monstearate, talc, sodium chloride, dried skim milk, glycerol, propylene glycol, water, ethanol, and the like. These compositions can take the form of solutions, suspensions, tablets, pills, capsules, powders, sustained-release formulations, and the like. Suitable pharmaceutical carriers are described in "Remington's Pharmaceutical Sciences" by E. W. Martin. The pharmaceutical compositions contain an effective therapeutic amount of the active agent together with a suitable amount of carrier so as to provide the form for proper administration to the host.

In summary, the antimalarial agent is especially useful as an agent for the prophylaxis against malaria infection of humans. It exhibits activity against malaria vectors, which is highly unusual and unexpected. The antimalarial agents exhibit marked suppression of the multiplication of malaria sporozoites in hepatocyte cultures and the livers of mice injected with malaria sporozoites. The antimalarial agent can reduce mortality and morbidity manifestations in humans, in particular by reducing the occurrence of infections.

What is claimed is:

1. A method of inhibiting malaria infection, wherein the method comprises administering genistein to a human in need thereof in an amount sufficient to inhibit infection of the human by malaria parasites.

2. The method of claim 1, wherein the malaria infection is caused by *Plasmodium falciparum, Plasmodium vivax, Plasmodium malariae*, or *Plasmodium ovale*.

3. The method of claim 1, wherein the genistein is formulated for oral, intravenous, inhalational, subcutaneous, injectable, or ingestible administration.

4. The method of claim 1, further comprising administering one or more antimalarial drugs.

5. The method of claim 4, wherein the antimalarial drug is quinine, quinidine, chloroquine, amodiaquine, mefloquine, halofantrine, pentaquine, isopentaquine, primaquine, tafenoquine, artemisinin, artemether, arteether, artesunate, dihydroartemisinin, 2,4-diaminopyrimidine, pyrimethamine, chloroguanide, sulfadoxine, sulfalene, dapsone, atoquavone, tetracycline, doxycycline, clindamycin, cyproheptadine, chlorpheniramine, desipramine, proguanil, lumefantrine, piperaquine, trimethoprim, pyronaridine, naphtoquine, fosmidomycin, or combinations thereof.

* * * * *